United States Patent
Noohi Bezanjani et al.

(10) Patent No.: US 12,073,013 B2
(45) Date of Patent: Aug. 27, 2024

(54) INTERACTION BETWEEN USER-INTERFACE AND MASTER CONTROLLER

(71) Applicant: Intuitive Surgical Operations, Inc., Sunnyvale, CA (US)

(72) Inventors: Ehsan Noohi Bezanjani, Los Gatos, CA (US); Keith Watza, Campbell, CA (US); Ashwinram Suresh, San Jose, CA (US); Brandon D. Itkowitz, San Jose, CA (US); Sean Duffy, San Jose, CA (US); Sarthak Ghosh, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 18/039,706

(22) PCT Filed: Nov. 22, 2021

(86) PCT No.: PCT/US2021/060400
§ 371 (c)(1),
(2) Date: May 31, 2023

(87) PCT Pub. No.: WO2022/119740
PCT Pub. Date: Jun. 9, 2022

(65) Prior Publication Data
US 2024/0111357 A1 Apr. 4, 2024

Related U.S. Application Data

(60) Provisional application No. 63/187,879, filed on May 12, 2021, provisional application No. 63/120,202, filed on Dec. 1, 2020.

(51) Int. Cl.
*G06F 3/01* (2006.01)

(52) U.S. Cl.
CPC .............. *G06F 3/011* (2013.01); *G06F 3/016* (2013.01)

(58) Field of Classification Search
CPC ....... A61B 5/7264; A61B 5/369; A61B 5/398; A61B 34/72; A61B 34/76;
(Continued)

(56) References Cited

U.S. PATENT DOCUMENTS 6,594,552 B1 7/2003 Nowlin et al.
10,786,315 B2 9/2020 Suresh et al.
(Continued)

FOREIGN PATENT DOCUMENTS

WO  WO-2019217882 A1  11/2019
WO  WO-2020188390 A1  9/2020

OTHER PUBLICATIONS

International Search Report and Written Opinion for Application No. PCT/US2021/60400, mailed May 3, 2022, 24 pages.
(Continued)

*Primary Examiner* — Nelson M Rosario
(74) *Attorney, Agent, or Firm* — Foley & Lardner LLP

(57) ABSTRACT

A method is provided to control actuation of a click event by a hand-actuated selector moveably mounted to a mount structure, comprising: in a first control state, imparting a maintaining force to the hand-actuated selector; in a second control state, imparting a haptic force to the hand-actuated selector that increases as a function of increasing displacement of the hand-actuated selector from the neutral displacement position; imparting a click event signal to cause an occurrence of the click event at a display system, in a third control state, imparting a haptic force to the hand-actuated selector that decreases in magnitude to a reduced magnitude.

15 Claims, 15 Drawing Sheets

(58) Field of Classification Search
CPC ..... A61B 2018/00297; A61B 2034/742; B25J 9/16; A61F 2/72; A61F 2/68; A61F 2/54; A61F 2002/5059; A61F 2002/5058; A61F 2002/5063; A61F 2002/5061; A61F 2/583; A61F 2/586; A61F 2002/587; A61F 2002/7615; A61F 2002/764; G06F 3/016; G06F 3/015; G06N 20/00; G06V 40/10; G06V 40/15; G06V 40/14

See application file for complete search history.

(56) References Cited

U.S. PATENT DOCUMENTS

| | | | |
|---|---|---|---|
| 2019/0099230 A1 | 4/2019 | Suresh et al. | |
| 2019/0151039 A1 | 5/2019 | Azizian | |
| 2019/0339804 A1* | 11/2019 | Gleeson | G06F 3/0488 |
| 2020/0129249 A1 | 4/2020 | Kelly et al. | |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

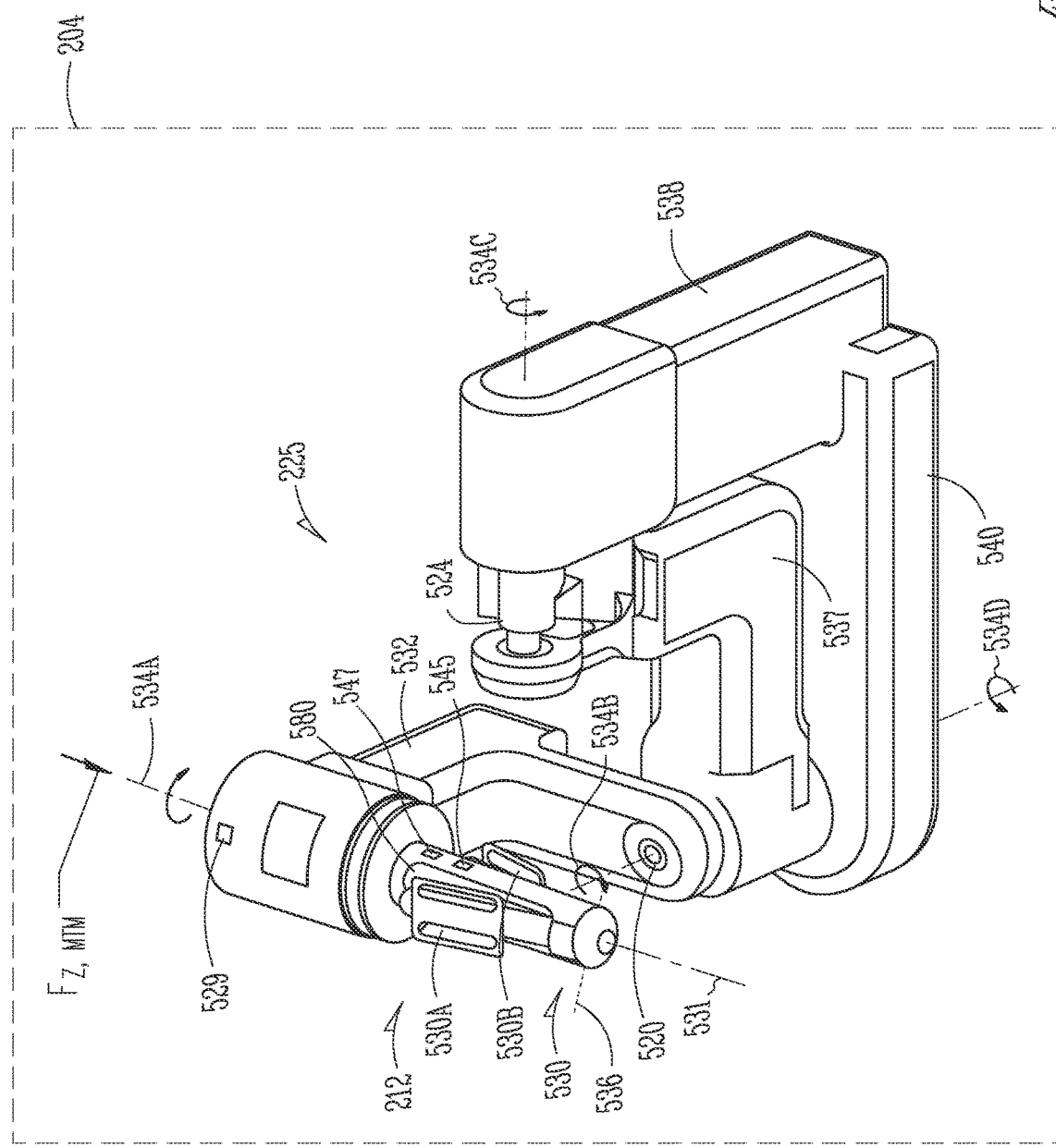

INTERACTION BETWEEN USER-INTERFACE AND MASTER CONTROLLER

CLAIM OF PRIORITY

This application is a U.S. National Stage Filing under 35 U.S.C. 371 from International Application No. PCT/US2021/060400, filed on Nov. 22, 2021, and published as WO 2022/119740 A1 on Jun. 9, 2022, which claims the benefit of priority to U.S. patent application Ser. No. 63/120,202, filed on Dec. 1, 2020, and to U.S. patent application Ser. No. 63/187,879, filed on May 12, 2021, each of which is incorporated by reference herein in its entirety.

BACKGROUND

Minimally invasive medical techniques are intended to reduce the amount of tissue that is damaged during diagnostic or surgical procedures, thereby reducing patient recovery time, discomfort, and deleterious side effects. Teleoperated surgical systems that use robotic technology (so-called surgical robotic systems) may be used to overcome limitations of manual laparoscopic and open surgery. Advances in telepresence systems provide surgeons views inside a patient's body, an increased number of degrees of motion of surgical instruments, and the ability for surgical collaboration over long distances. Teleoperated control over surgical robotic technology typically involves user interaction with hand-controlled manipulators to control motion of surgical instruments and involves user interaction with finger-controlled selectors to trigger occurrence of robotic system events. Haptic feedback can improve a user's teleoperated control over surgical robotic technology.

SUMMARY

In one aspect, a method is provided to control actuation of a click event by a hand-actuated selector moveably mounted to a mount structure. Sensors sense amount of displacement distance of the hand-actuated selector from a neutral position. While the hand-actuated sensor is at a displacement distance less than a first threshold distance from the neutral position, controlling one or more motors according to a first control state to impart a maintaining force. While the hand-actuated sensor is at a displacement distance between a first threshold distance from the neutral position and a second threshold distance from the neutral position, motors are controlled according to a second control state to impart a haptic force to the hand-actuated selector that increases as a function of increasing displacement of the hand-actuated selector from the neutral displacement position. Once the hand-actuated sensor has met the second threshold distance from the neutral position, a click event signal is imparted to cause an occurrence of the click event at a display system. Also, once the hand-actuated sensor has met the second threshold distance from the neutral position, the one or more motors are controlled according to a third control state to reduce magnitude of the haptic force imparted to the hand-actuated selector to a reduced magnitude that is less than a maximum magnitude of the haptic force imparted during the second control state.

In another aspect, a method is provided to control motion of a cursor in a first two-dimensional (2D) plane based upon motion of a user input device in a second 2D plane and based upon motion of a hand-actuated selector moveably mounted to the user input device. The cursor is caused to move in the first 2D plane, to following motion of the user input device in the second 2D plane according to a constant movement ratio, while the hand-actuated selector moves relative to the user input device at a rate less than a first threshold rate. The cursor is caused to move in the first 2D plane, to follow motion of the user interface device in the second 2D plane according to a movement ratio that decreases as a function of increasing rate of movement of the hand-actuated selector relative to the user input device in response to rate of movement of the hand-actuated selector relative to the controller being between the first threshold rate and a second threshold rate. The cursor is caused to move in the first 2D plane, to follow motion of the user input device in the second 2D plane according to motion ratio that increases as a function of decreasing rate of movement of the hand-actuated selector relative to the user input device, in response to rate of movement of the hand-actuated selector relative to the user input device decreasing below the second threshold rate.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which:

FIG. 6A is an illustrative perspective showing details of an example user input device that acts as a mount for a hand-actuated selector.

DESCRIPTION OF EMBODIMENTS

The following description is presented to enable any person skilled in the art to create and use systems and methods of a medical device simulator. Various modifications to the embodiments will be readily apparent to those skilled in the art, and the generic principles defined herein may be applied to other embodiments and applications without departing from the scope of the inventive subject matter. Moreover, in the following description, numerous details are set forth for the purpose of explanation. However, one of ordinary skill in the art will realize that the inventive subject matter might be practiced without the use of these specific details. In other instances, well known machine components, processes and data structures are shown in block diagram form in order not to obscure the disclosure with unnecessary detail. Flow diagrams in drawings referenced below are used to represent processes. A computer system may be configured to perform some of these processes. Modules within flow diagrams representing computer-implemented processes represent the configuration of a computer system according to computer program code to perform the acts described with reference to these modules. Thus, the inventive subject matter is not intended to be limited to the embodiments shown but is to be accorded the widest scope consistent with the principles and features disclosed herein.

Figure 1:
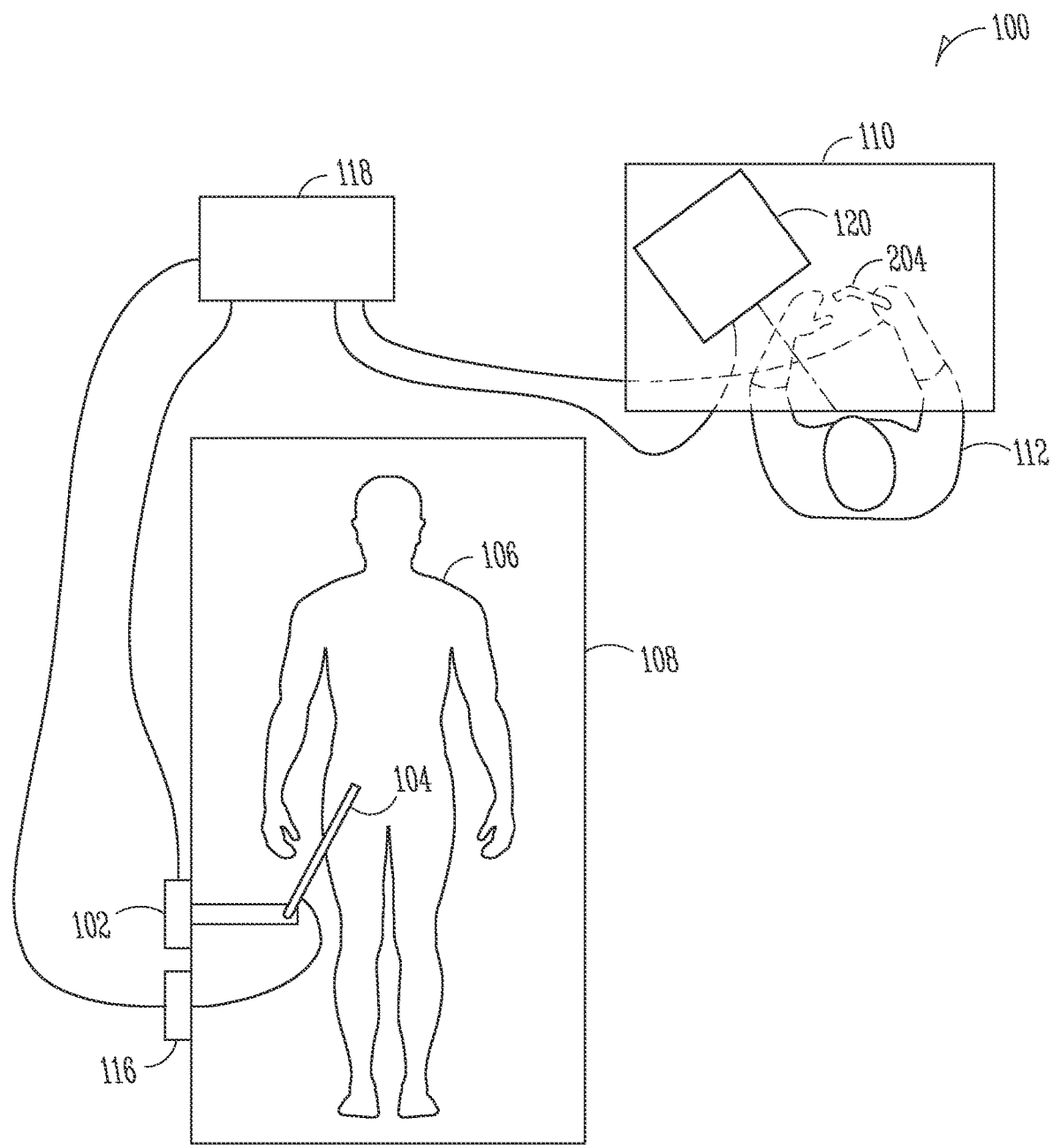
FIG. 1 is an illustrative schematic drawing illustrating an example teleoperated surgical system.

Teleoperated Surgical System FIG. 1 is a schematic drawing illustrating an example teleoperated surgical system 100. The teleoperated surgical system 100 includes an instrument manipulator assembly 102 that may include one or more linkages, for manipulating operation of a surgical instrument 104 in response to user input control in performing various procedures on a patient 106. The instrument manipulator assembly 102 is mounted to or located near an operating table 108. A user input control system 110 allows a user 112 to view the surgical site and to control the instrument manipulator assembly 102.

In alternative embodiments, the example teleoperated surgical system 100 can include more than one instrument manipulator assembly 102. The exact number of manipulator assemblies can depend on the surgical procedure and the space constraints within the operating room, among other factors.

The user input control system 110 can be located in the same room as the operating table 108. However, it should be understood that a user 112 such as a surgeon or clinician can be located in a different room or a completely different building from the patient 106. The user input control system 110 generally includes a visions system that includes a visualization system 116 and a display system 120 and includes a motion system that includes or more user input devices 204, one or more instrument manipulator assemblies 102 and an instrument motion and input device haptic feedback haptic controller (referred to herein as a "input controller") 118.

The one or more user input devices 204 are operatively coupled to one or more instrument manipulator assemblies 102 for controlling motion of one or more instruments 104 in response to user input provided at the user input devices 204. In an example teleoperated surgical system 100, the one or more user input devices 204 and the one or more instrument manipulator assemblies 102 are communicatively coupled to input controller 118. An example motion controller processes user input received at the one or more user input devices 204 to control motion of the one or more instrument manipulator assemblies 102. An example input controller 118 produces haptic feedback signals used to adjust the state of haptic forces at the one or more user input devices 204 based upon motion of the one or more instrument manipulator assemblies 102 and/or based upon motion of the user input devices 204.

The user input devices 204 may include any number of a variety of input devices, such as gravity-balanced arms, joysticks, trackballs, gloves, trigger-grips, twistable knobs, twistable grips, sliders, levers push buttons, or the like. In some embodiments, the user input devices 204 may be provided with the same degrees of freedom as the associated surgical instruments 104 to provide the user 112 with telepresence, or the perception that the user input devices 204 are integral with the instrument 104 so that the user 112 has a strong sense of directly controlling the instrument 104. In some embodiments, the user input devices 204 is a manual input device that moves with six degrees of freedom or more, and which may also include an actuatable handle or other control feature (e.g., one or more buttons, switches, etc.) for actuating instruments (for example, for closing grasping jaws, applying an electrical potential to an electrode, delivering a medicinal treatment, or the like).

The visualization system 116 provides a concurrent two-dimensional (2D) or three-dimensional (3D) image of a surgical site to the user 112 as the user 112 operates one or more instruments. The visualization system 116 may include a viewing scope assembly such that visual images may be captured by an endoscope positioned within the surgical site. The visualization system 116 may be implemented as hardware, firmware, software or a combination thereof, which interact with or are otherwise executed by one or more computer processors, which may include processors of a control system 110.

A display system 120 may display a visual image of the surgical site and surgical instruments 104 captured by the visualization system 116. The display system 120 and the user input devices 204 may be oriented such that the relative positions of the visual imaging device in the scope assembly and the surgical instruments 104 are similar to the relative positions of the surgeon's eyes and hands so the operator (e.g., user 112) may manipulate the surgical instrument 104 with the user input devices 204 as if viewing a working volume adjacent to the instrument 104 in substantially true presence. By "true presence" it is meant that the presentation of an image is a true perspective image simulating the viewpoint of an operator that is physically manipulating the surgical instruments 104.

The instrument motion input controller 118 includes at least one processor circuit (not shown) and typically a plurality of processor circuits for effecting control between the user input devices 204, the user input control system 110, and the display system 120. The input controller 118 also includes software programming instructions to implement some or all of the methods described herein. While the input controller 118 is shown as a single block in the simplified schematic of FIG. 1, the input controller 118 may comprise a number of data processing circuits (e.g., on the user input devices 204 and/or on the user input control system 110). Any of a wide variety of centralized or distributed data processing architectures may be employed. Moreover, one or more processing circuits can be implemented at virtual machines. Similarly, the programming code may be implemented as a number of separate programs or subroutines or may be integrated into a number of other aspects of the teleoperated systems described herein. In various embodiments, the input controller 118 may support wireless communication protocols such as Bluetooth, IrDA, HomeRF. IEEE 802.11, DECT, and Wireless Telemetry.

An example input controller 118 may include servo controllers to provide haptic force and/or haptic torque feedback at a user input device 204 based upon forces and torques sensed at a surgical instrument 104 to the user input devices 204. An example input controller 118 may include servo controllers to provide haptic force and/or haptic torque feedback to a user input device 204 based upon forces and torques sensed at the input device the user input device 204. Any suitable conventional or specialized servo controller may be used. A servo controller may be separate from, or integral with, the instrument manipulator assembly 102. A servo controller also may be separate from, or integral with, the user input device 204. In an example medical system, an example servo controller and a manipulator assembly 102 are provided as part of a robotic arm cart positioned adjacent to the patient 106. In an example medical system, an example servo controller and a user input device 204 are positioned adjacent to a user providing input at the user input device 204.

For the purposes of this document, the surgical instrument 104 may be referred to as a "controlled device".

In an example teleoperated surgical system 100, an input controller 118 controls at least one controlled device 104 (e.g., "surgical instrument") and may control movement of one or more linkages 102-1 of one or more instrument manipulator assemblies 102. An example instrument manipulator assembly 102 includes one or more motors coupled to control motion of end effector associated with an instrument 104. An example instrument manipulator assembly 102 includes one or more motors coupled to control motion of one or more end effectors coupled to an instrument 104. The linkages 102-1 may be referred to as a set-up structure, which includes one or more links coupled with joints 102-2 that allows the set-up structure to be positioned and held at a position and orientation in space. The motors coupled to control motion of one or more end effectors of an instrument an are further coupled to the surgical instrument 104 so as to advance the surgical instrument 104 into a naturally or surgically created anatomical orifice and to move the surgical instrument 104 and to move an instrument's end effector in multiple degrees of freedom that may include three degrees of linear motion (e.g., x, y, and z linear motion) and three degrees of rotational motion (e.g., roll, pitch, yaw). The motors of an example manipulator assembly 102 may be configured to actuate an effector of the surgical instrument 104 such as an articulatable effector for grasping tissues in the jaws of a biopsy device or an effector for obtaining a tissue sample or for dispensing medicine, or another effector for providing other treatment as described more fully below, for example. U.S. Pat. No. 6,671,581, entitled, Camera Referenced Control in a Minimally Invasive Surgical Apparatus, which is incorporated by reference, contains further information on camera referenced control in a minimally invasive surgical apparatus.

In an example teleoperated surgical system 100, for training purposes, the display system 120 may display a virtual environment simulating a surgical site within a patient. The virtual environment may include various biological structures in addition to the surgical instrument 104. The user 112 operates a virtual instrument within the virtual environment to train, obtain certification, or experiment with various skills or procedures without having the possibility of harming a real patient.

In either a live surgery or a simulated surgical procedure, the display system 120 may be used to present a user-interface to a user (e.g., the user 112). In an embodiment, the display system 120 provides a 3D view, such as a stereo display. In another In an example teleoperated surgical system, the display system 120 is used to project a 3D image, such as from a high-definition endoscope camera. A user-interface may be displayed as an overlay, such as by using a translucent interface, or may be displayed in place of the view of the surgical field.

Figure 2A:
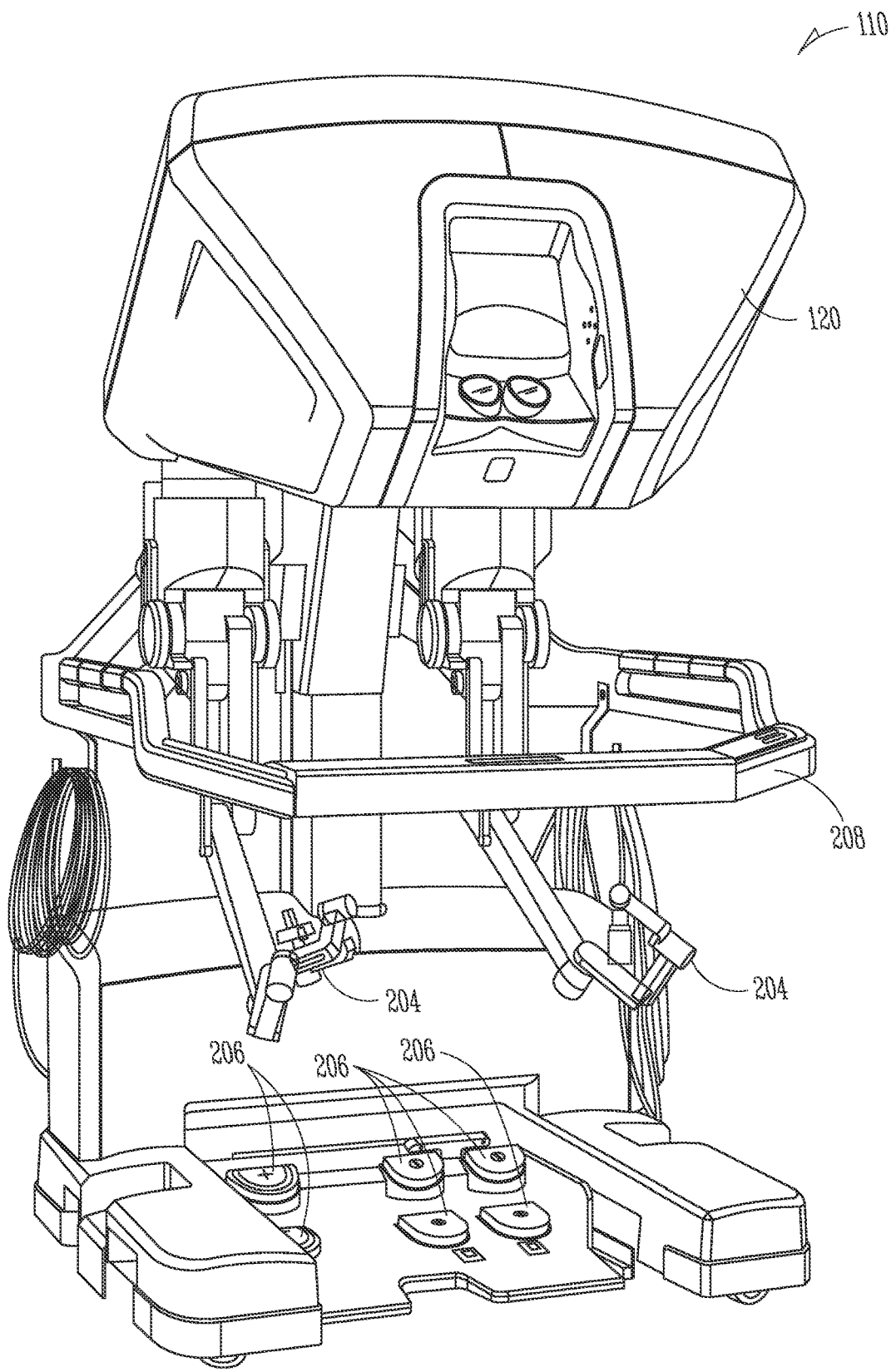
FIG. 2A is an illustrative drawing illustrating an example user input control system, according to an embodiment.

FIG. 2A is a drawing illustrating an example user input control system 110. A user may sit at the user input control system 110 and may access a display system 120, and the user input devices 204, and footswitch panel 206. The footswitch panel 206 can act as a clutch, for example, that enables the user to switch between performing various tasks, such as swapping between various surgical instruments or controlling video or camera features. While seated at the user input control system 110, the user may rest their arms on an armrest 208. When operating in a live surgery, the display system 120 displays the surgical field as captured from a camera inserted through a small opening to the surgical site, sometimes referred to as a portal or a cannula. For training purposes, a simulated environment may be displayed on the display system 120, where the simulated environment may be a stereoscopic display of a surgical site and virtual controlled devices (e.g., surgical instruments). As the user moves the user input devices 204, a virtual surgical instrument may move in a corresponding fashion in the stereoscopic display.

Figure 2B:
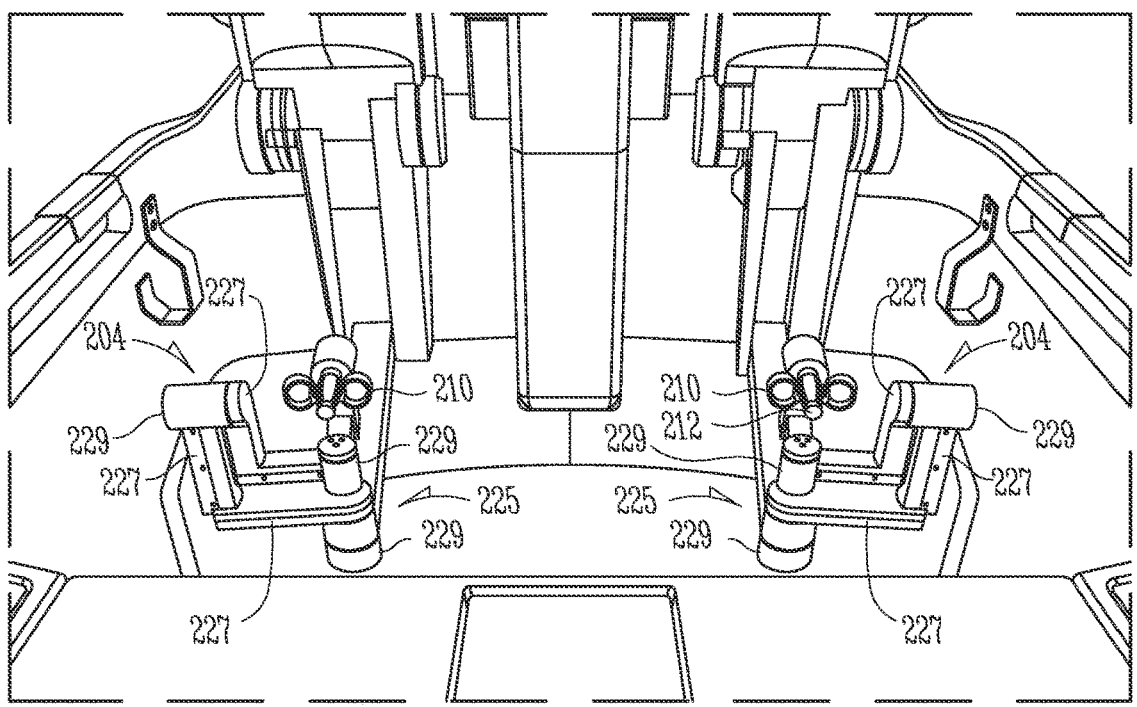
FIG. 2B is an illustrative drawing illustrating an example instrument motion controller of an example user input control system.

FIG. 2B is an illustrative drawing showing example user input devices 204 operatively coupled to the user input control system 110. The example user input devices 204 include a gimbal mount 225, which includes an articulated arm portion including a plurality of links 227 connected together by pivotal joints 229. The user grips finger loops 210 by positioning his or her thumb and index finger over a displaceable hand-actuated selector 212, such as a pincher push button, for example. In an example user input device 204, a user's thumb and index finger are typically held on the displaceable hand-actuated selector 212 by straps threaded through slots to create the finger loops 210. The example selector 212 includes first and second grip buttons 503a, 503b, explained below with reference to FIG. 5, that are spaced apart at a distance so that they can be gripped between a user's thumb and index fingers with a user's thumb engaging one grip button and the user's index finger engaging the other, for example. At least one of the grip buttons is moveable to reduce displacement distance between the grip buttons in response to a user squeezing force imparted to the grip buttons engaged between them. The joints 229 of the example user input device 204 are operatively connected to motors, or the like, to provide for, e.g., force feedback, gravity compensation, and the like. Furthermore, appropriately positioned sensors, e.g., encoders, or potentiometers, or the like, are positioned on each joint 229 of the example user input device 204, so as to enable joint positions of the example user input device 204 to be determined by the user input controller 118 to control motion of one or more instruments operatively coupled to the user input devices or to control haptic feedback forces imparted to the one or more input devices 204.

An example teleoperated surgical system 100 includes two user input devices 204, each with two finger loops 210 for which the user may insert an index finger and thumb of a respective hand. The two user input devices 204 may each control a surgical instrument or a virtual surgical instrument. The user may be provided software or hardware mechanisms to swap between multiple instruments for one or both instrument motion controller 204. For example, a user may be provided three instruments, such as two forceps and a retractor. One or both of the forceps may be an energy instrument able to cauterize tissue. The user may first use the forceps at each instrument motion controller 204, then switch the right example user input device 204 to control the retractor to expose a section of the surgical field, and then switch the right example user input device 204 back to the forceps to continue cutting, probing, or dissecting tissue.

While using the example user input devices 204, the user is provided with full 3D range of motion (x, y, and z axis) along with rotational motion (roll, pitch, yaw) in addition to pinching motion with the index and thumb (or any two fingers inserted into the loops 210). As such, by moving the appropriate user input device 204, the user is able to manipulate the corresponding surgical instrument through a full range of motion.

Figure 2C:
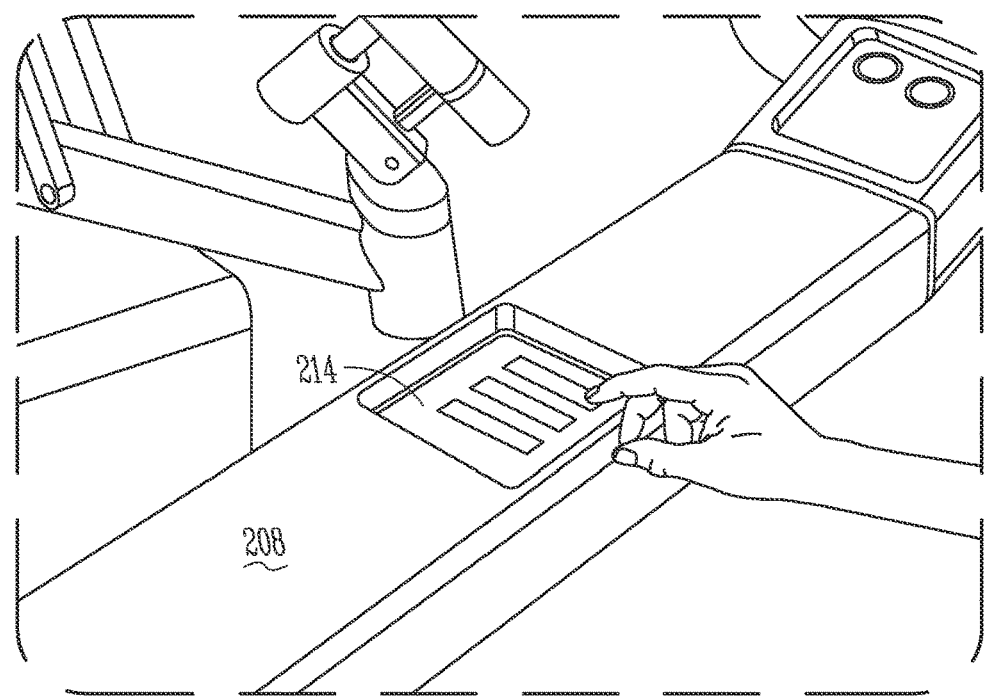
FIG. 2C is an illustrative drawing illustrating an example armrest of an example user input control system.

FIG. 2C is a drawing illustrating an armrest 208 of a user input control system 110, according to an embodiment. The armrest 208 may include one more touch control, such as touchscreens, soft buttons, mechanical buttons, or the like. In the example illustrated in FIG. 2C, a single touchscreen 214 is shown through which the user may configure various video, audio, or other system settings.

Overview of Graphical User-Interface Control

During operation, a user may be presented a user interface at various times. For example, a user interface may be presented to allow the user to choose from a selection of training modules. As another example, a user interface may be presented to allow the user to configure various aspects of the operation of the user input control system 110. When the user has one or both hands operating an example user input device 204, it may be inconvenient to have to release example user input device 204 and then operate another input mechanism, such as a touchscreen interface integrated into the armrest 208 of the user input control system 110.

Figure 3:
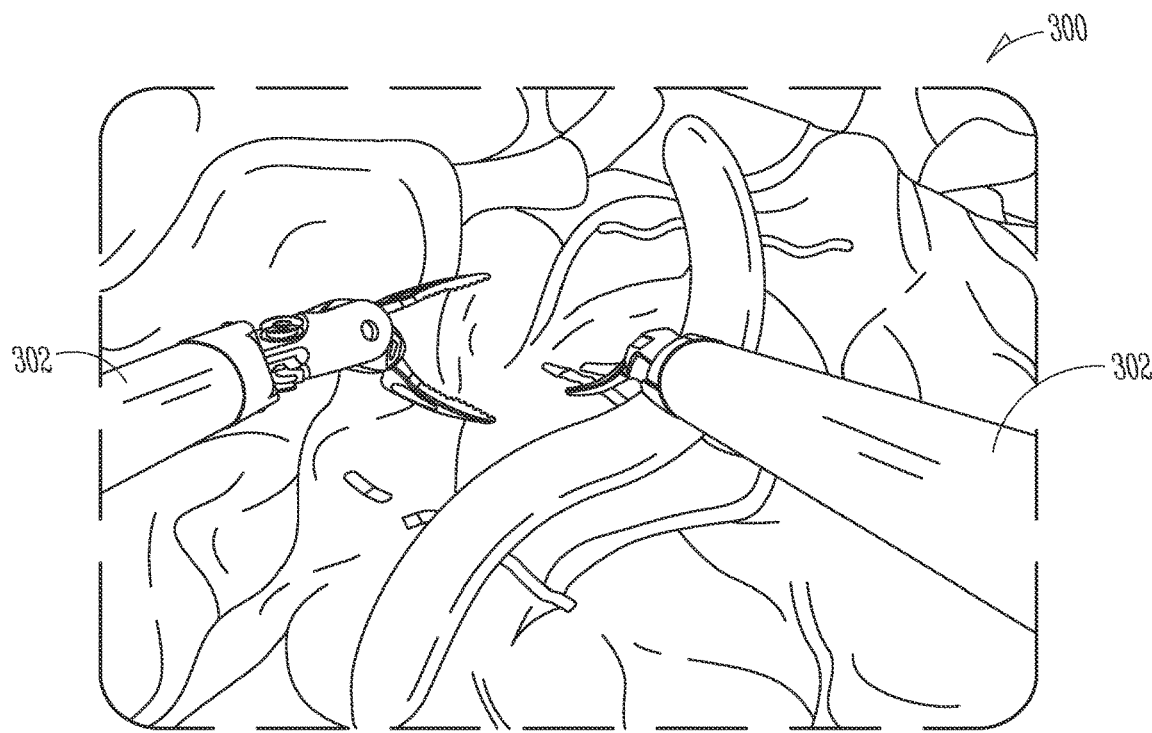
FIG. 3 illustrates an example virtual surgical site viewable at a display system viewing plane during 3D mode operation.

FIG. 3 is an illustrative drawing showing a virtual surgical site displayed by the display system 120 operating in a 3D mode. The virtual surgical site 300 may be displayed on the display system 120 and includes two virtual controlled devices 302. When operating in this mode, the user input devices 204 is able to move in 3D in free space (within the boundaries of the virtual surgical site 300) to control the controlled devices 302. In a second mode, the user input devices 204 are restricted to movement within a virtual surface that can be planar or have a contour such as a gentle curvature, for example. The second mode can be used, for example, to present a graphical user interface that includes control elements (e.g., buttons, knobs, sliders, pull-down menus) that can be controlled using the user input devices 204 as pointing and clicking devices, for example. The second mode can be used, for example, to present 2D images such as pre-operative images for example. The second mode is useful to provide an operating space for the user input devices 204 that can be roughly aligned with the 2D virtual surface.

Figure 4A:
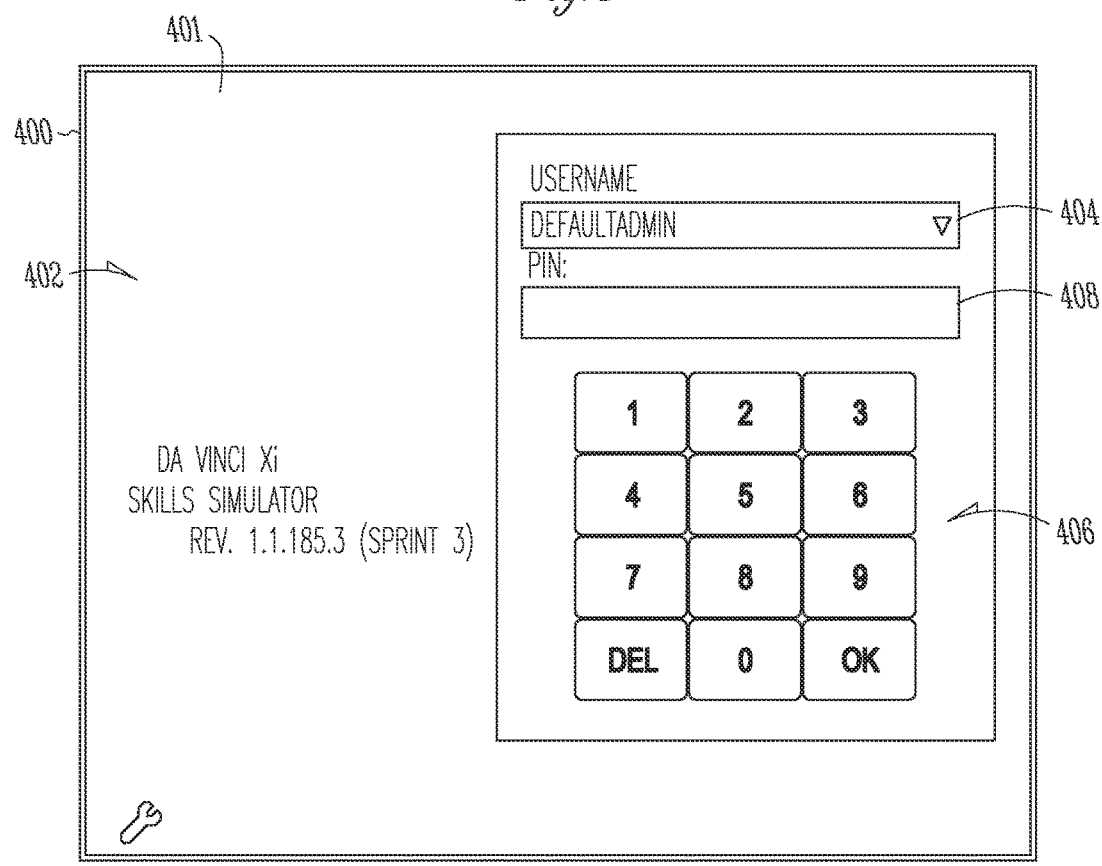
FIGS. 4A-4D illustrate example graphical user interfaces viewable at a display system viewing plane during 2D mode operation.

FIG. 4A illustrates a first example graphical user interface screen display 400 displayed by the display system 120 operating in a 2D mode. The first graphical user interface 400 is optionally displayed as an overlay to the surgical site view or as a standalone interface. A cursor 402 is displayed within the first user interface 400 and is used to activate one or more user interface controls, such as buttons, sliders, option lists, etc. The cursor 402 may be controlled by a user input device 204. Using servo controls coupled to the user input device 204, the user may be provided with haptic feedback to provide a sensation of touching the first user interface 400. For example, when the user uses an input device 204 to effect virtual motion of a user interface control structure, such to select a virtual button, slide a virtual slider control, or move a virtual dial displayed in the user interface, for example, the user input device 204 motors coupled to the input device 204 may cause the input device 204 to vibrate, shake, impart a reactive force to oppose the user's motion, or otherwise react to the actuation of the user interface control to provide the user with sensory feedback. FIG. 4A illustrates an example login display 401, which includes a user-selectable menu-pulldown arrow 404. A user can move the cursor 402 to overlay the menu selection arrow 402, whereupon the user can select the overlaid menu selection arrow 402 by actuating (e.g., by squeezing) the displaceable hand-actuated selector 212, to impart a click event that causes occurrence of surgical system action such as display of a pulldown menu (not shown) in a display system 120 or energizing an electrosurgical instrument (not shown) within a surgical site 300, for example.

As used herein, a "click event" a click event may refer to a displacement of the displaceable hand-actuated selector 212 relative to the user input device 204 that causes the controller 118 to send a signal to the display system to select or actuate a selectable element in a user interface display. As used herein, a "click event" also may refer to a displacement of the displaceable hand-actuated selector 212 relative to the user input device 204 that causes the controller 118 to send a signal to one or more motors of the manipulator assembly to cause motion of one or more of a real or virtual instrument, instrument end effector, or manipulator linage. In an example teleoperated surgical system 100, a click event causes selection or actuation of a selectable element in a user interface display during 2D operation of the system 100 and a click event causes motion of a real or virtual component of a manipulator assembly during 3D mode operation of the system 100.

For example, during 2D mode operation, a user can use the cursor to select a menu item from the pulldown menu. The login screen 401 also includes a keypad with multiple control elements (i.e. virtual buttons) 406. A user can move the cursor 402 to overlay a keypad control element, whereupon the user can select the overlaid keypad button by squeezing the displaceable hand-actuated selector 212, to impart a click event that causes display of the selected element in a display region 408. In an example teleoperated surgical system 100, the keyboard control panel can be used to select an energy level electrosurgical instrument, for example.

Figure 4B:
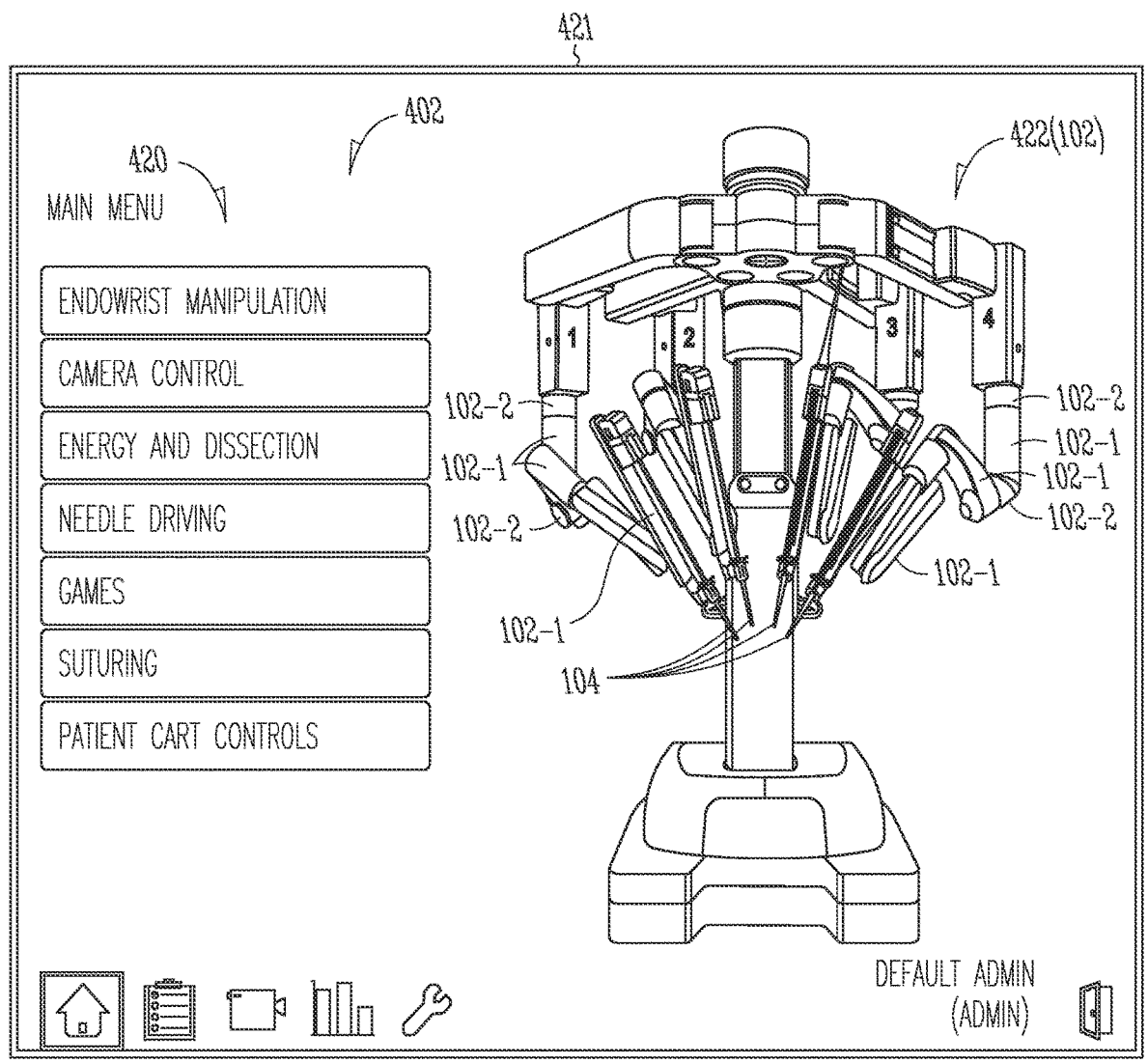

FIG. 4B illustrates an example second graphical user interface screen display 421 that includes multiple control elements menu 420 and instrument manipulator assembly image 422 that shows an example instrument manipulator assembly 102. In an example teleoperated surgical system 100, a user can use the user input device 204 in a 2D operation mode to select a control element from within the control elements menu 420, whereupon a a different menu (not shown) corresponding to the selected menu element is displayed.

Figure 4C:
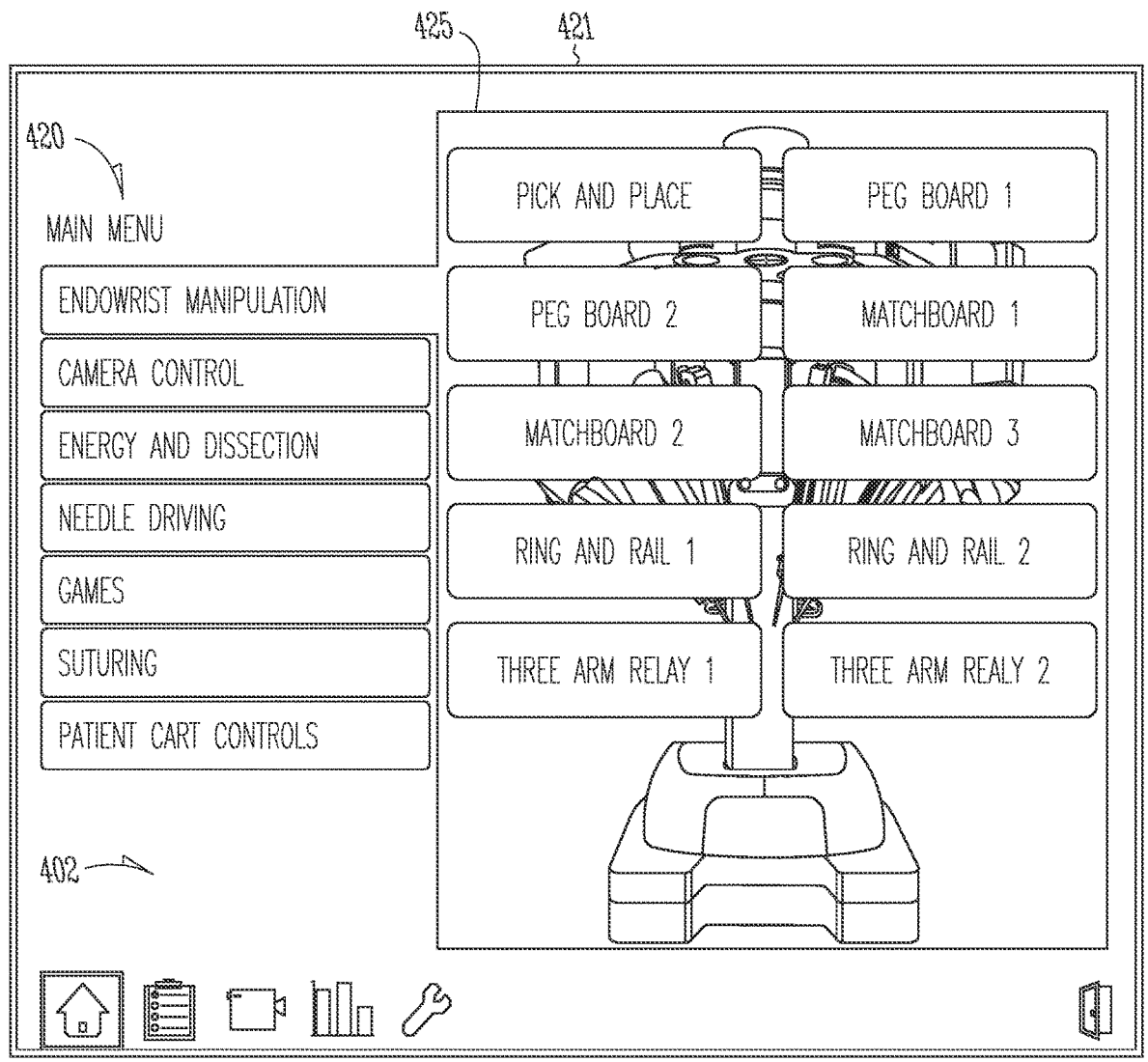

FIG. 4C illustrates the example second graphical user interface screen display 421 of FIG. 4B with an Endowrist Manipulation menu 425 displayed overlaying the instrument manipulator assembly image 422 in response to a user's selection of the Endowrist Manipulation control element of FIGS. 4B-4C.

Figure 4D:
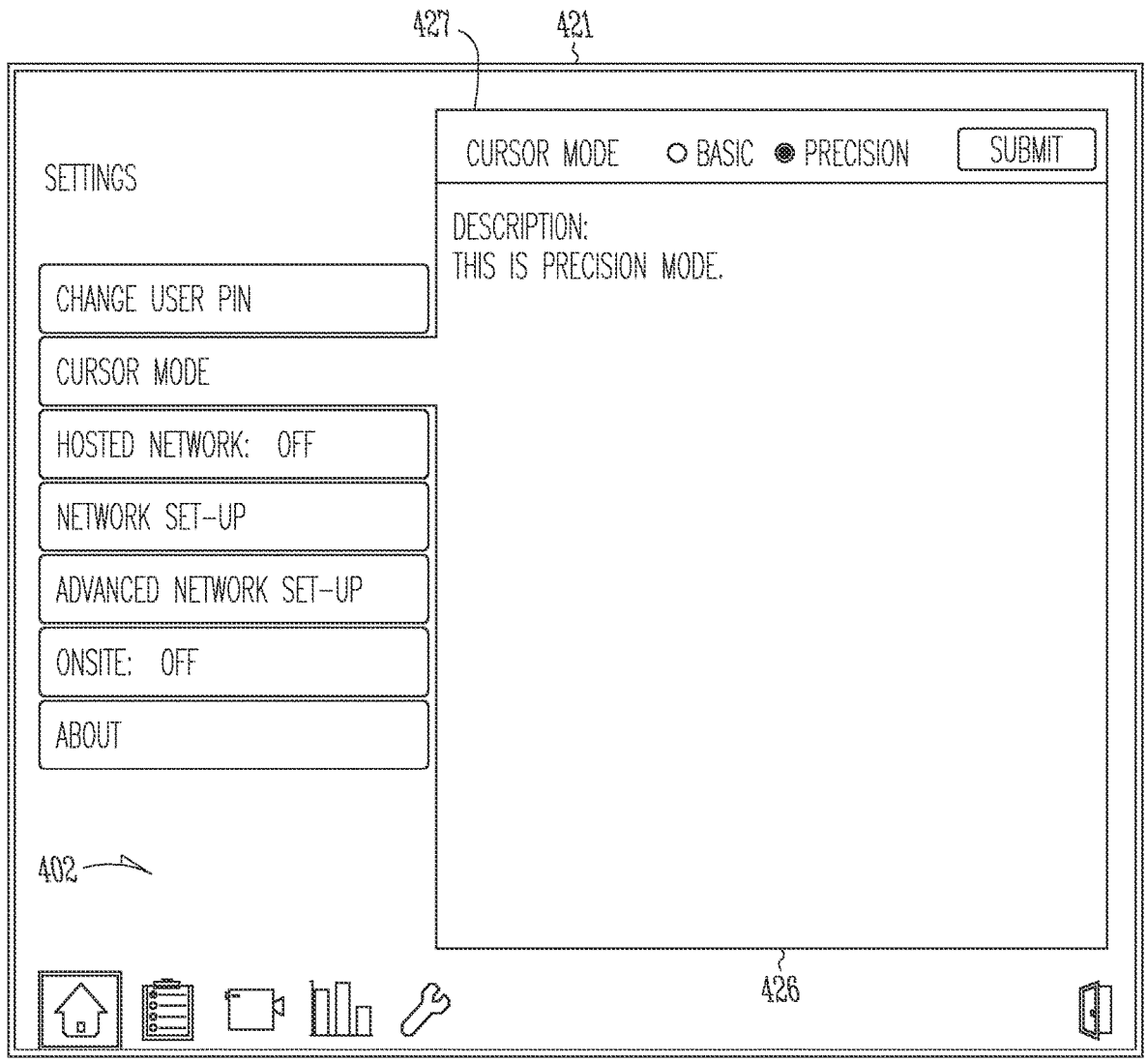

FIG. 4D illustrates the example second graphical user interface screen display 421 of FIGS. 4B-4C with a Cursor Mode menu 427 displayed overlaying the instrument manipulator assembly image 422 in response to a user's selection of the Cursor Mode control element of FIGS. 4B-4D. It is understood that more or fewer screens may be used in the second user interface 400.

The example first and second graphical user interface displays 400, 402 are presented as a 2D interfaces. As such, when the user is controlling a cursor in the graphical user interface, the user input devices 204 are constrained to a 2D region. In contrast, when in a surgical simulation mode (e.g., a first mode), the user input devices 204 are permitted full or nearly full 3D freedom of motion. However, in a graphical user interface mode (e.g., a second mode), the user input devices 204 are constrained to 2D motion. The 2D motion can be constrained to a planar region or to a region have a gentle curvature, such as a gentle convex curvature for example. A 2D region to which motion of the user input devices 204 are constrained can be oriented in space such that the user's hands and user input devices 204 are at approximately the same angle as that displayed in the display system 202. Such correlation may assist the user to orient their hands in 3D space with respect to the graphical user interface displayed.

Figure 5:
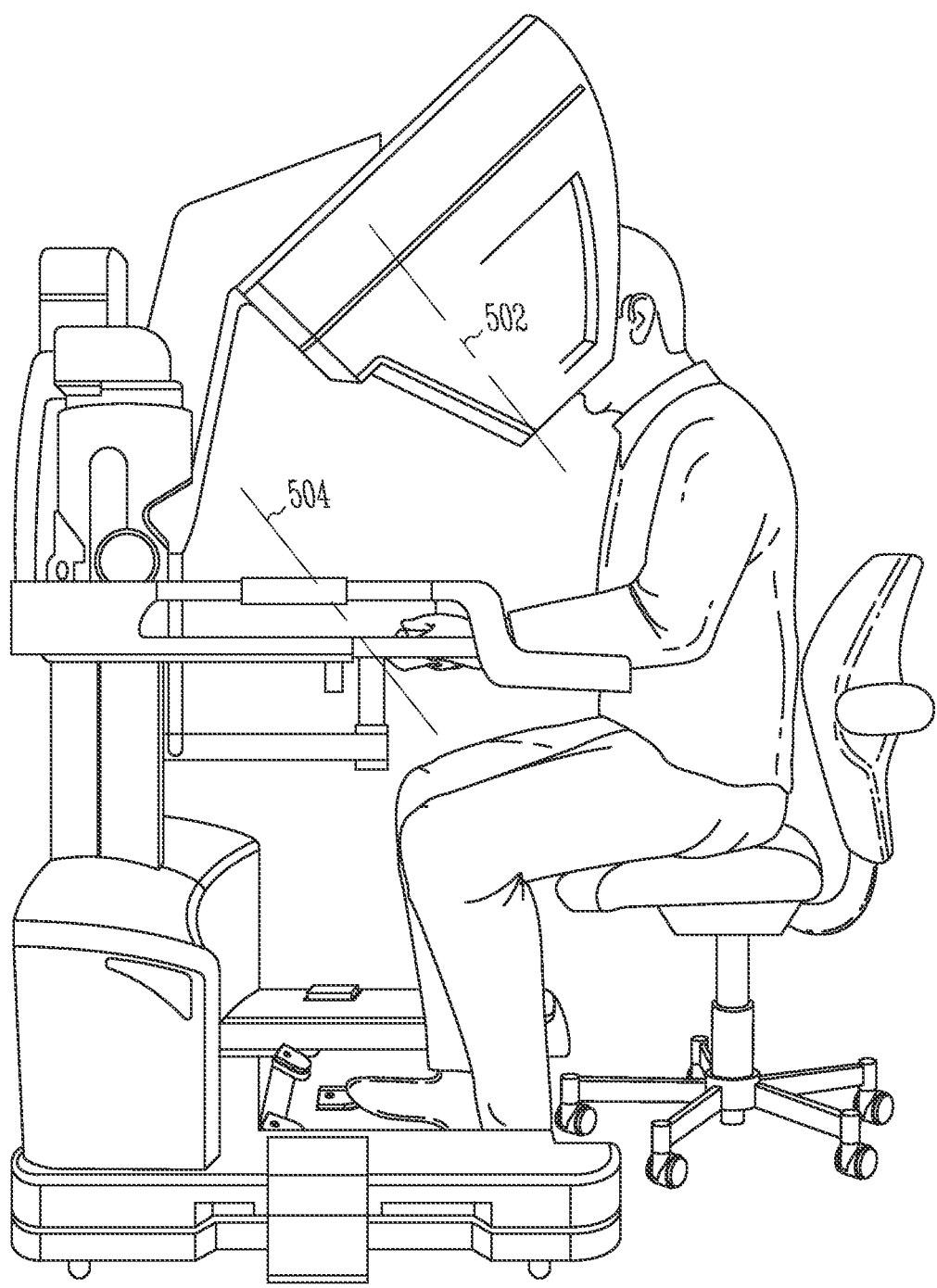
FIG. 5 is an illustrative diagram showing an example viewing plane and an example haptic plane.

An example is illustrated in FIG. 5, which shows a viewing plane 502 and a haptic plane 504. The viewing plane 502 represents a planar region in which graphical user interface images are presented to a user by the user in the display system 202 in which the example first and second graphical user interface screen displays 400, 421 of FIGS. 4A-4D can be displayed, for example. Cartesian coordinate locations in the viewing plane 502 correspond to cartesian coordinate locations in the haptic plane 504. A user can select a control element displayed at a cartesian coordinate location in the viewing plane 502 by moving one of the user input devices 204 to a corresponding cartesian coordinate location in the haptic plane and clicking at that corresponding location. More particularly, motion of a cursor in the graphical user interface displayed in the viewing plane 502 follows motion of a user input device 204 in the haptic plane 504. Thus, as a user causes a user input device 204 to move within the 2D haptic region 504, a cursor is displayed moving correspondingly within one of the first and second graphical user interface screen displays 400, 421 displayed within the visual image region 502. In the second mode, user hand motion causes corresponding motion of a user input device 204 within the 2D region 504 that causes corresponding motion of a cursor image in the viewing region 502. To select a desired control element displayed in the visual image region 502, a user can engage a user input device 204 with his or her hand and move the hand to cause corresponding motion of the user input device 204 so as to cause corresponding motion of the cursor so as to visually align with the cursor with the desired control element. With the cursor aligned, the user then can select the desired control element, for example, by imparting a finger motion to impart motion to a displaceable hand-actuated selector 212 to affect a click-to-select (a 'click") user interface action. In response to the click, a processor circuit implements an action associated with the selected control element.

The user input devices 204 are constrained within the 2D haptic planar region 504. When a user attempts to move a user input device 204 "up" or "down" with respect to the z-axis of the haptic plane 504, the user may encounter resistance from such movement. Should the user change the orientation of the viewing plane 502, such as with a display configuration setting, then the haptic plane 504 may adjust to maintain an approximately parallel orientation with respect to the viewing plane 502. In various embodiments, the haptic plane may be oriented at a fixed or dynamic angle offset with respect to viewing plane. Alternatively, the haptic plane may be oriented with a fixed or dynamic angle offset with respect to the ground. A user may also alter the constraints, for example, the position or orientation of the haptic plane.

One or more processor circuits are configured to scale movement of a user input device 204 when imparting corresponding movement to a controlled device in the first (3D) mode and to impart corresponding movement to a cursor in the second (2D) mode. In the first mode, scaling allows a user to perform intricate medical procedures with greater ease than conventional open surgery. Scaling includes scaling a commanded movement of the user input device 204 according to a scale factor before imparting corresponding movement to a controlled device or to a cursor. Scaling considers changes in velocity and position of the user input device 204 and converts these to corresponding scaled changes in position of a controlled device or cursor. Scale factor is adjustable and can be different during operation in the first and second modes. In the second mode, for example, the scale factor can be unity (i.e. no scaling). U.S. Pat. No. 7,843,158, entitled "Medical robotic System Adapted to Inhibit Motions Resulting in Excessive End Effector Forces, which is incorporated by reference, contains further information about scaling.

User Input Device with Hand-Actuated Click Selector

FIG. 6A is an illustrative perspective showing details of an example user input device 204 that acts as a mount for a displaceable hand-actuated click selector 212. The example user input device 204 is mounted upon a gimbal mount assembly 225 and is coupled to the input controller 118 of FIG. 2A. The gimbal mount 225 includes a controller motion sensor (first sensor) 529 to sense motion of the overall controller 225. An example user input device 204, can include multiple controller motion sensors 529 (only one shown) to sense motion of the controller in multiple degrees of freedom. An example user input device 204 includes an example displaceable hand-actuated selector 212 that includes a pincher mount member configured as an elongaged handle 530, which includes a longitudinal axis 531. The example displaceable hand-actuated selector 212 is formed integral with the example user input device 204, such that the hand-actuated selector 212 moves in unison with 2D motion of the user input device 204 and such that the hand-actuated selector 212 moves in unison with 3D motion of the user input device 204. The example hand-actuated selector 212 includes first and second articulable pincher grip buttons 530a, 530b mounted upon the handle 530. The handle 530 acts as a mount member to mount the grip buttons 530a, 530b of the hand-actuated selector 212.

The first and second grip buttons 530a, 530b of the hand-actuated selector 212 upstand at an incline from opposite sides of the handle 530.

The first and second grip buttons 530a, 530b are secured to the handle 530 to articulate relative to the handle 530. The first and second grip buttons 530a, 530b are inclined relative to the handle 530 with their distal ends spaced closer together and their proximal ends spaced farther apart. As used herein the term "proximal" indicates a location closer to a manipulator support structure and more distant from a patient anatomy, and the term "distal" indicates a location more distant from the manipulator support structure and closer to the patient. The first and second grip buttons 530a. 530b have an angle α between their distal ends that may vary according to forces exerted upon them by a user. In an example teleoperated surgical system 100, when a user exerts no pinching force to move the grip buttons 530a, 530b closer to one another, the grip buttons 530a, 530b are in a neutral position. In an example user input device 204, the grip buttons 530a, 530b are maximally displaced from one another in the neutral position. In an example user input device 204, when the grip members are in the neutral position, the angle α is an acute angle. In an example user input device 204, in the neutral position, one or more motors 545 impart a haptic counter-force to the grip buttons 530a, 530b that resists a user-exerted force to move the grip buttons 530a, 530b toward one another, and a user must overcome this haptic counter-force to move the grip buttons 530a, 530b toward one another. In an alternative example user input device 204, in the neutral position, a biasing member member (not shown), such as a spring, provides a reactive force to resist displacement of the grip buttons 530a, 530b toward one another, and a user must overcome this reactive force to move the grip buttons 530a, 530b toward one another.

In an example user input device 204, one or more motors 545 cause the grip buttons 530a, 530b to move to the neutral position on a first condition (i) when a user imparts no force to the grip buttons 530a, 530b and on a second condition (ii) when the grip buttons 530a, 530b have a displacement position distance between them that meets a prescribed threshold. In an alternative example user input device 204, a biasing member (not shown), such as a spring, causes the grip buttons 530a, 530b to move to the neutral position on a first condition (i) when a user imparts no force to the grip buttons 530a, 530b and on a second condition (ii) when the grip buttons 530a, 530b have a displacement position distance between them that meets a prescribed threshold. In an example user input device 204, the second condition occurs when the grip buttons 530a, 530b have a displacement position distance between them that is less than a second grip threshold (TG2) distance explained below. A click event causes a surgical system to launch an action such as a display action at the display system 120 or an instrument action within the surgical site 300 at or before the grip buttons 530a, 530b reach a click event displacement position greater than the second grip threshold (TG2) distance. Thus, by the time the displacement distance position is in the first control state 776 of the graph 770 described below, an action has been launched in response to the decreased displacement distance between the grip buttons 530a, 530b. For example, a control element in the control elements menu 420 of the second graphical user interface screen display 421 of FIGS. 4B-4C will have been selected and a screen display corresponding to the selected control element will be displayed. For example, if the click event is the selection of the Endowrist manipulation control element then the Endowrist Manipulation menu 425 of FIG. 4C will be displayed.

In an example user input device 204, a user can impart force upon the respective grip buttons 530a, 530b in respective directions toward the handle 530 to reduce the displacement between them until the girp members abut the handle mount 530, which acts as a stop surface, whereupon there is no displacement between the grip buttons and the handle mount. More specifically, in accordance with some embodiments, the first and second grip buttons 530a, 530b are secured to the handle to pivot about a master pivot axis 536. One or more motors 545 or other biasing member urges the grip buttons 530a, 530b apart. In an example user input device 204, one or more motors 545 are configured to impart a variable haptic force in a direction radially outward from the mount member 530 toward the grip buttons 530a, 530b during user-imparted radially inward direction motion of the grip buttons 530a, 530b toward the handle 530. In an example user input device 204, the one or more motors 545 can include a single motor (not shown) that can impart haptic forces to both grip buttons 530a, 530b. In an alternative example user input device 204, the one or more motors 545 can include can include a first motor (not shown) to impart haptic force to a first grip button 530a and can include a second motor (not shown) to impart haptic foce to the second grip button 530b. The handle 530 includes one or more displacement sensors (a second sensor) 547 such as a Hall effect device to sense movement of the grip buttons 530a, 530b along the first path and their displacement from the neutral displacement position. Finger loops (not shown) can be attached to the handle to avoid slipping from the grip buttons. A wide variety of grip button structures might be used within the scope of the disclosure, including any surgical instrument handles, optionally including rigid or flexible loops for the thumb and/or fingers, for example. Control relationships between the grip buttons and controlled devices is explained in more detail in U.S. Pat. No. 6,594,552, entitled, "Grip Strength with Tactile Feedback for Robotic Surgery", the full disclosure of which is expressly incorporated by this by reference.

In the first (3D) operating mode, the user input device 204 and the grip buttons 530a, 530b are operatively coupled through kinematices, for example, to control motion of a controlled device 104 in response to 3D motion of the user input device 204 and motion of the grip buttons 530a. 530b about the master pivot axis 536. In the second (2D) operating mode, the controller 204 and the grip buttons 530a, 530b are are operatively coupled to control 2D cursor movement within the viewing plane 502 and control element selection within the viewing plane 502.

In an example teleoperated surgical system 100, the one or more motors are selectably configured to impart to the grip buttons 530a. 530b a variable haptic force in a radially outward direction from the handle 530. A user can use his or her fingers to impart forces to the grip buttons 530a, 530b to urge them toward the handle 530 located between them and toward one another so as to cause them to move closer together. As explained below, in the second (2D) mode, a user can use the hand-actuated selector 212 to effect a click event to select a graphical user interface control element, by imparting finger forces in a radially inward direction toward the handle 530 to overcome the neutral resistance and motor-controlled haptic force, and urge the grip buttons 530a, 530b toward one another. As explained below, a variable haptic force is imparted to the grip buttons 530a, 530b of the hand-actuated selector 212 to provide haptic feedback to indicate when an occurrence of a click event within the viewing plane 502 has occurred.

An example user input device 204 includes a four-degree of freedom gimbal mount 225 to allow a user to rotate of the actuatable mount member handle 530 about three axes, axis 534a, axis 534b, and axis 534c. During operation in the first (3D) mode, a physical or virtual controlled device, such as an instrument 104, follows 3D motion of the user input device 204. During operation in the second (2D) mode, a controlled user interface element, such as a cursor, within the 2D viewing region 502 follows 2D motion of the user input device 204 within the 2D region 504.

More particularly, the handle mount 530 portion of the user input device 204 is coupled to a first elbow-shaped link 514 by a first pivotal joint 16. First link 532 is coupled to a second elbow-shaped link 537 by a pivotal joint 520. Second link 537 is pivotally coupled to a third elbow-shaped link 538 by a pivotal joint 524. In some embodiments, motors of arm 538 and gimbal 225 are capable of actively applying positional and orientational forces to mount member handle 530, thereby providing tactile feedback to the surgeon. The gimbal 225 includes links 532, 537, 538. Gimbal 225 is mounted to platform 540 so as to rotate about axis 534d, and links 532, 537, 538 define additional axes 534a, 534b and 534c. Handle 530 is mounted to gimbal 225 by an actively driven joint for motion about axis 534d. Hence, gimbal 225 provides four driven orientational degrees of freedom, including a redundant orientational degree of freedom. Gimbal 225, arm 538, and the driving motors for these joints are described in more detail in U.S. Pat. No. 6,714,839, entitled "Master Having Redundant Degrees of Freedom", the full disclosure of which is expressly incorporated by this by reference.

Figure 6B:
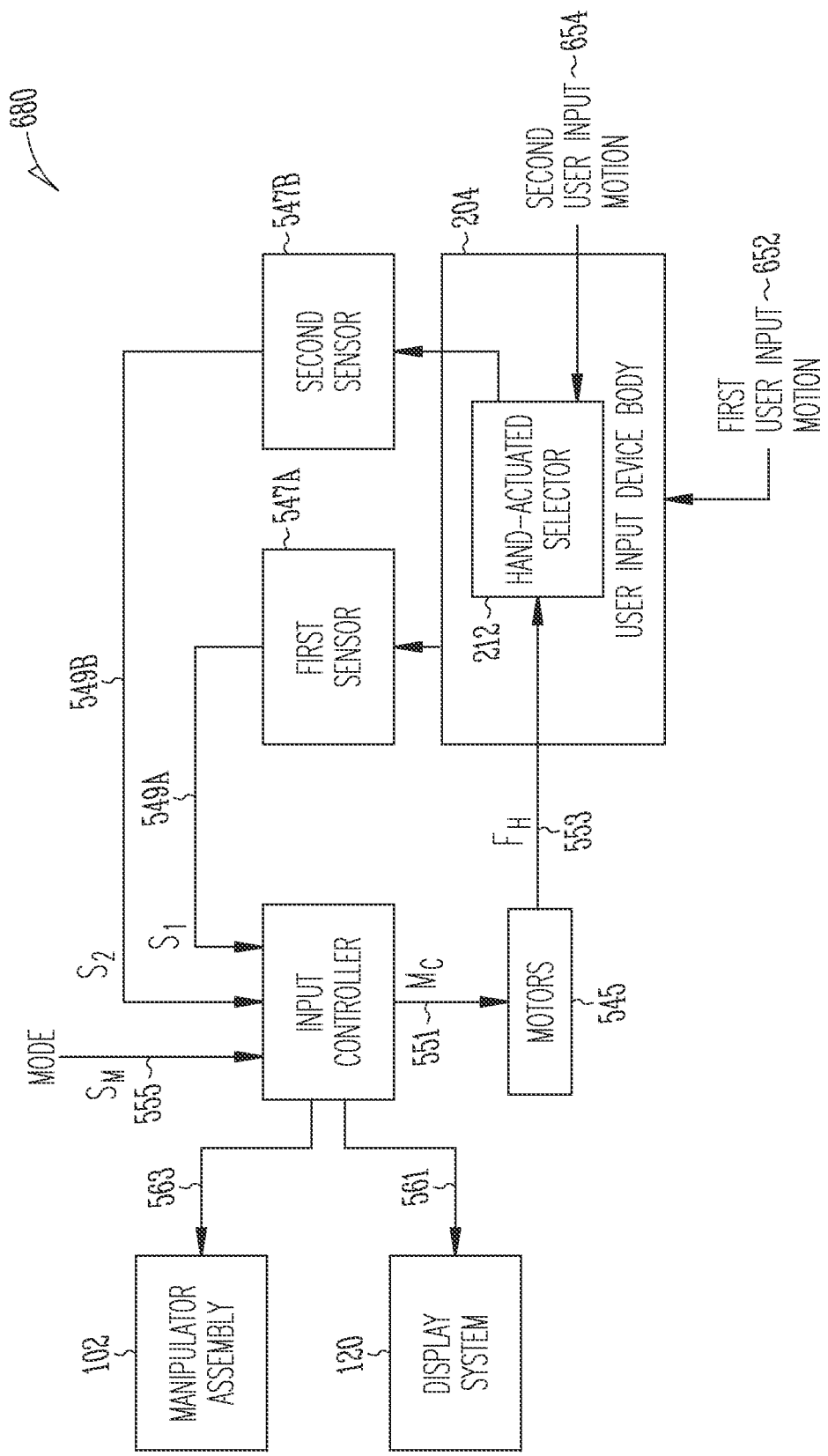
FIG. 6B is an illustrative functional block diagram showing a control system to control receive user input at a user input device that includes a hand-actuated selector and to impart haptic feedback at the user input device.

FIG. 6B is an illustrative functional block diagram showing a control system 680 to control receive user input at a user input device 204 that includes a hand-actuated selector 212 and to impart haptic feedback at the user input device 204. An input controller 118 is coupled to control the manipulator assembly 102 and is coupled to control the display system 120. A user input device 204 is configured to receive first user input motion 652, such as user hand motion, that imparts motion to the overall user input device 204. A hand-actuated selector 212 is moveably mounted to the user input device 204 is configured to receive second user input 654, such as user finger motion, that imparts motion to the hand-actuated selector 212 relative to the user input device 204. One or more first sensors 547a are configured to sense motion of the overall user input device 204 and to provide corresponding first sensor signals ($S_1$) 549a to the input controller 118. One or more second sensors 547b are configured to sense motion of the hand-actuated selector 212 relative to the user input device 204 and to provide corresponding second sensor signals ($S_2$) 549b to the input controller 118. One or more motors 545 are coupled to receive motor control signals 551 from the input controller 118 and to impart haptic feedback forces 553 to the hand-actuated selector 212. The input controller 118 is configured to provide motor control signals ($M_C$) 551 to one or more motors 545, based upon one or more of the first and second sensor signals 549a. 549b, to cause the one or more motors to to impart haptic feedback force ($F_H$) 553 to the hand-actuated selector 212.

A user can provide a mode select signal ($S_M$) 555 to cause the input controller 118 to operate in one of a 3D mode and a 2D mode. In the 3D mode, the displaceable hand-actuated selector 212 can move in 3D in concert with motion of the user input device 204 in response to first user input motion 652 and can be displaced relative to the user input device 204 in response to second user input. In the 2D mode, the the displaceable hand-actuated selector 212 can move in 2D in concert with the user input device 204 in response to first user input and can be displaced relative to the user input device 204 in response to second user input motion 654.

In the 3D mode, the input controller 118 controls the manipulator assembly 102, including one or more motors (not shown) controlling operation of one or more of an instrument 104, an instrument end effector, and a manipulator link in response to motion imparting user input causing one or more of displacement of the overall user input device 204 and displaceable hand-actuated selector 612 relative to the user input device 204 on which the selector is mounted. In the 2D mode, the input controller 118 controls the display system 120, including a graphical user interface screen display including one or more control elements such as, menu, cursor, slider, knob, or button, for example, in response to user input causing one or more of displacement of the overall user input device 204 and displaceable hand-actuated selector 612 relative to the user input device 204.

The first displacement sensor 547a is coupled to sense displacement of the overall user input device 204 and to provide the corresponding first sensor signals 549a to the input controller 118 indicating displacement of the user input device 204. A second sensor 547b is coupled to sense displacement of the hand-actuated selector 212 relative to the user input device 204 and to provide the corresponding second sensor signals 549b to the input controller 118 indicating displacement of the the hand-actuated selector 212 relative to the user input device 204 on which the selector 212 is moveably mounted. The input controller 118 includes one or more processor circuits configured with executable instructions to provide control signals to control the manipulator assembly 102 in response to first and second sensor signals when in the 3D mode and to provide control signals to control the display system 120 in response to one or more of the first and second sensor signals when in the 2D mode. The input controller 118 is further configured to provide the motor control signals 553 to the one or more motors 545 to impart haptic feedback force $F_H$ to the hand-actuated selector 212 in based upon one or more of the first and second sensor signals 549a, 549b.

Haptic Feedback to Indicate Click Event

Figure 7:
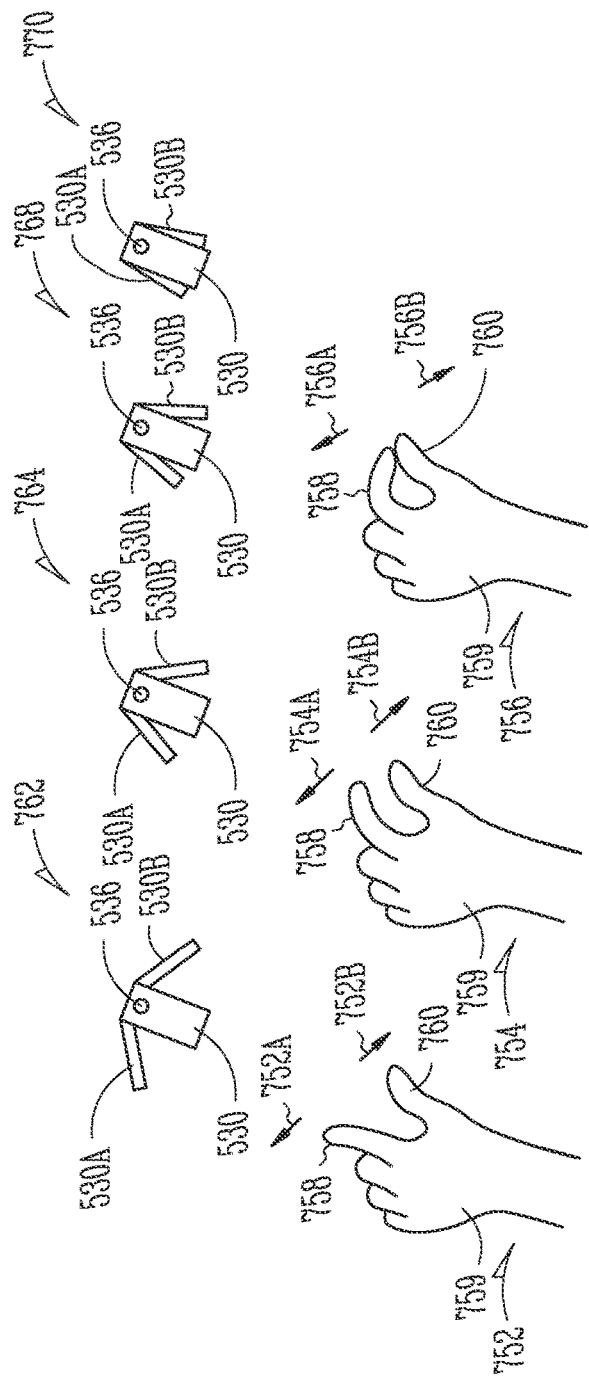
FIG. 7 is an illustrative drawing showing a first control function curve representing haptic force versus displacement of a displaceable hand-actuated selector position during a click event and also showing a time-aligned sequence of grip button displacements and a time-aligned with a sequence of hand formations.
Figure 7:
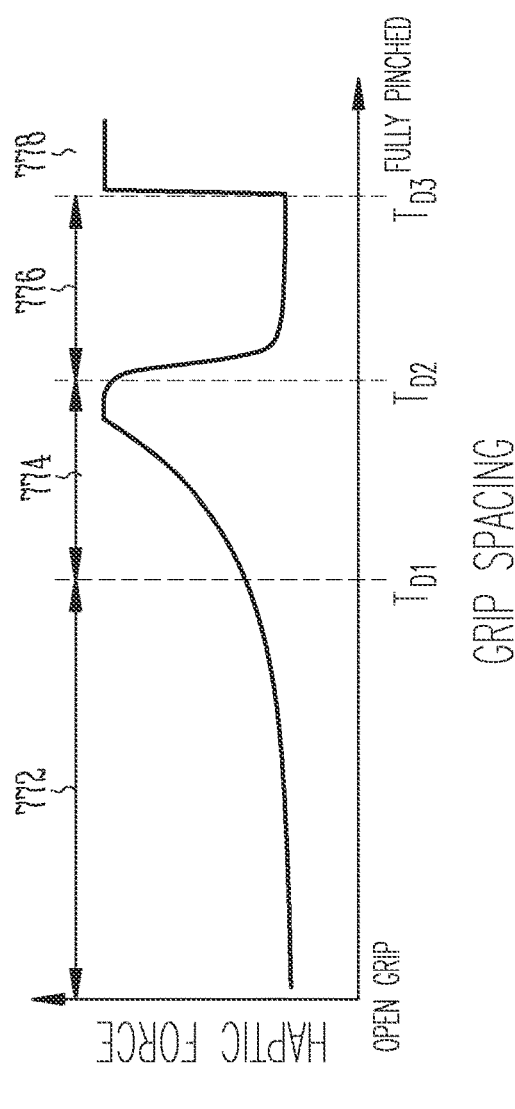

FIG. 7 is an illustrative drawing showing a first control function curve 720 representing haptic force versus displacement of a displaceable hand-actuated selector 212 position during a click event that is time-aligned with a sequence of grip button displacements and with a sequence of hand formations. The example user input device 204 of FIG. 6A comprises a handle 530 that acts as a mount on which a pair of opposed grip buttons 530a, 530b are mounted. As explained above, alternative example hand actuated selectors include gravity-balanced arms, joysticks, trackballs, gloves, trigger-grips, twistable knobs, twistable grips, sliders, levers push buttons, or the like. A user can cause a click event by imparting a second user input motion that causes a prescribed displacement of the displaceable hand-actuated selector 212. For the hand-actuated selector 212 of FIG. 6A, for example, example, a user can cause a click event by decreasing a displacement of distance of grip buttons 530a, 530b from a neutral position displacement to a click event completion position displacement distance. In the example user input device 204 of FIG. 6A, each grip button is equally displaced from the user input device's handle mount 530 throughout movement of the grip buttons 530a, 530b between open and closed positions, although the displacement distance between the grip buttons decreases as the grip buttons 530a, 530b move from open to closed positions and increases as the grip buttons 530a, 530b move from closed to open positions. Moreover, in the example user input device 204 of FIG. 6A, each individual grip button 530a, 530b has a displacement distance between it and the user input device's handle mount 530 that decreases as that grip button moves from a neutral displacement position to a click event completion displacement position and that increases as that grip button moves from the click event displacement position to the neutral displacement position.

FIG. 7 shows an example sequence of displacement positions of the grip buttons 530a, 530b of the example hand-actuated selector 212 of FIG. 6A during a pincher closure due to a second user input motion 646 caused by a user's fingers during a click event is represented by the sequence of user finger positions 752, 754, 756. FIG. 7 also shows a corresponding example sequence of displacement positions 762, 764, 768, 770 of grip buttons 530a, 530b of the example hand-actuated selector 212 of FIG. 6A. For simplicity and clarity of illustration, an example user's fingers 758, 760 and the sequence of finger positions 752, 754, 756 are shown separated from the respective grip buttons 530a, 530b that they contact and the corresponding sequence of grip button displacement positions 762, 764, 768, 770, although it will be understood that in actual use, respective fingers 758, 760 are in contact with the respective grip buttons 530a, 530b. For example, in an actual example use, a cursor finger 758 contacts a first grip button 530a and a thumb 760 contacts a second grip button 530b.

FIG. 7 shows an example sequence of displacement positions 762, 764, 768, 770 of the grip buttons 530a, 530b of FIG. 6A that each corresponds to a different movement distance, relative to the user input device's handle 530, travelled by the grip buttons during a click event. Thus, at an illustrative displacement distance indicated by grip button displacement position 762 and corresponding finger position 752, the grip buttons have traveled the first (shortest) distance, relative to the user input device's handle 530, in the illustrative sequence. At an illustrative displacement distance indicated by grip button displacement position 764 and corresponding finger position 754, the grip buttons have traveled a second distance, relative to the user input device's handle 530, that is greater than the first distance. At an illustrative displacement distance indicated by grip button displacement position 768 and corresponding finger position 756, the grip buttons have traveled a third distance that is greater than the combined first and second distances, relative to the user input device's handle 530, At an illustrative displacement distance indicated by grip button displacement position 770 and corresponding finger position 756, the grip buttons have traveled a fourth distance relative to the user input device's handle 530, that is greater than the first, second, and third distances.

FIG. 7 also shows a corresponding sequence of finger positions of a hand 759 that imparts a second user input motion 654 to the grips 530a. 530b. The finger position sequence starts with fully open finger position 752, followed by partially closed/partially open finger position 754, which is followed by a substantially closed finger position 756. A sequence of grip button displacement positions about a handle mount 530 is shown. The grip button sequence starts with fully open grip button displacement position 762, followed by partially closed/partially open grip button displacement position 764, followed by near-fully closed grip button displacement position 768, followed by fully closed grip button position 770.

FIG. 7 includes an illustrative curve 770 representing a control function curve that controls a combined click event triggering and haptic feedback control function that is implemented using the hand-actuated selector 212, the second sensor 547b, the input controller 118, the one or more motors 545, and a stop surface such as an input device's handle 530. The input controller 118 includes one or more processor circuits programmed with executable instructions to implement the control function 700. The control function 770 controls triggering of a click event and controls haptic feedback force imparted in response to second user input motion 654 displacing the hand-actuated selector 212. More particularly, the input controller 118 is configured to implement the control function in response to second sensor signals $S_2$ provided by the one or more second sensors, to control triggering of a click event at the display system 120 or at the manipulator assembly 102 and to cause the one or more motors 545 to impart a haptic force to the hand-actuated selector 212. According to the control function 770, to trigger a click event, a user must displace the hand-actuated selector 212 by at least a prescribed displacement distance. Moreover, according to the control function 770, a haptic feedback force is imparted to the hand-actuated selector 212 while the user is displacing the hand-actuated selector 212. The haptic feedback force indicates to the user, both a build up to and a triggering of a click event in response to the user's increasing displacement of the hand-actuated selector 212. The stop surface imparts an abrupt reactive force that stops further displacement of the hand-actuated selector 212 after a prescribed amount of further displacement following triggering of a click event.

The control function curve 770 has multiple states. A first control state 772 is a neutral or at rest state in which displacement of the hand-actuated selector 212 is less than a first threshold displacement $T_{D1}$. In the case of the user input device 204 of FIG. 6A, in the first control state 772, the grip buttons 530a, 530b are displaced from the handle 530 by a distance that is between a maximal displacement in a neutral position and the first threshold distance $T_1$. In an example teleoperated surgical system 100, in the first control state 772, a resilient member imparts a maintaining force upon the hand-actuated selector 212 to urge it in the neutral displacement position. In the case of the user input device 204 of FIG. 6A, in the first control state 772, a biasing member, such as a spring member, urges the the grip buttons 530a, 530b maximally displaced from one another and from the handle 530, while the input controller 118 causes the one or more motors to impart a constant, zero, force. In an alternative example teleoperated surgical system 100, in the first control state, the input controller 118 causes the one or more motors 545 to impart a resilient maintaining force to the hand-actuated selector 212 to urge it to the neutral displacement position. In the alternative first control state 772, the one or motors 545 are controlled to produce a spring-like maintaining force to maintain the hand-actuated selector 212 in the neutral displacement position. In the alternative first control state 772, the one or motors provide a force to move the return the hand-actuated selector 212 to the neutral position in response to a user's imparting a force to overcome the maintaining force that causes the selector 212 to be displaced by less than first displacement threshold distance and the user's then removing that force. While in the first control state 772, a user may impart motion to the hand-actuated selector to displace it somewhat from the neutral position provided that the displacement is the first threshold distance $T_{D1}$. A magnitude and direction of such maintaining force in relation to a user's fingers for the example user input device of FIG. 6A is represented by arrows 752a, 752b. The first and second directions extend radially outward from the longitudinal axis 531 of the handle 530.

A second control state 774 is a haptic feedback force build-up state in which haptic force increases at a first rate relative to increasing displacement of the hand-actuated selector 212. The second control state 774 includes displacements of the hand-actuated selector 212 that meet the first threshold distance $T_{D1}$ but do not yet meet a second threshold distance $T_{D2}$. During the second control state 774, the one or more second sensors 547b sense increasing displacement of the hand-actuated selector 212 from the neutral position and send corresponding second senor signal values $S_2$ to the input controller 118 to report the increasing displacement. The input controller 118, in turn, produces motor control signals 553 to cause the one or more motors 545 to impart haptic force the hand-actuated selector 212 that increases at a first rate relative to increasing displacement of the hand-actuated selector 212 form the neutral position. The first rate can be linear or non-linear provided that the rate is such that the user has time to recognize and react to the tactile sensation of increasing haptic force by following through with or aborting an imminent click event. In the case of the example user input device 204 of FIG. 6A, the grip buttons 530a, 530b are displaced from one another by smaller and smaller amounts as they are increasingly displaced from their more widely spaced apart neutral positions. The build up of haptic force, which increases in magnitude at a first rate relative to increasing displacement of the hand-actuated selector 212 during the second control state 774, provides a tactile indication, or warning, to a user of imminence of a click event: the greater the magnitude, the closer the current displacement is to causing an occurrence of a click event. The second rate is selected such that a user has time to react in response to an indication of imminence of a click event, so for example, the user can make a conscious decision to continue with the displacement and follow through with a click event or to stop the displacement and abort the click event. Thus, the increasing haptic feedback during the second control state 774 warns the user that a click event is increasingly imminent as the with increasing displacement of the hand-actuated selector 212.

In the example user input device 204 of FIG. 6A, a magnitude of a second feedback force during the second control state is represented by the lengths of arrows 754a, 754b. Grip button 530a imparts force 754a in a first direction to index finger 758, and grip button 530b imparts force 754b in a second direction opposite to the first direction to thumb 760. The first and second directions extend radially outward from the longitudinal axis 531 of the handle 530 and from the longitudinal axis 531 of the handle 530. It will be appreciated that in order to move the grip buttons 530a, 530b closer together during the second control state 774, a user's fingers 758, 760 impart respective displacement forces in directions opposite to the haptic force directions 754a, 754b. The user-imparted forces have magnitudes sufficiently large to overcome the haptic forces 754a, 754b. Also, it will be understood that magnitude of the haptic forces 754a. 754b imparted by the respective grip buttons 530a, 530b at any example instant in the second control state 774, is greater forces 752a, 752b during the maintaining force during the first control state 772, as represented by the length of arrows 754a. 754b being greater than the length of the arrows 752a, 752b.

A third control state 776 is a click event trigger state that occurs when displacement of the hand-actuated selector 212 meets the second threshold distance $T_{D2}$. The second sensors 547b send to the input controller 118 second sensor signals indicating when the displacement of the hand-actuated selector 212 reaches the second threshold displacement $T_{D2}$ from the neutral position.

An example input controller 118, when operating in a 2D mode, in response to the hand-actuated sensor 212 reaching the second threshold displacement $T_{D2}$, sends a click event triggering signal to the display system 120 causing selection of a visual UI control element overlayed by a cursor 402 in the control elements menu 420, for example. An example input controller 118, when operating in a 3D mode, in response to the hand-actuated sensor 212 reaching the second threshold displacement $T_{D2}$, sends a click event triggering signal to the manipulator assembly 102 causing actuation of one or more motors (not shown) to actuate a link or an instrument end effector, for example.

Additionally, an example input controller 118, when operating in either a 2D mode or a 3D mode, in response to the hand-actuated sensor 212 reaching the second threshold displacement $T_{D2}$, imparts a motor control signal $M_C$ on line 551 causing the one or more motors 545 to impart a step-down haptic feedback force to the hand-actuated selector 212. The step-down haptic feedback force decreases haptic feedback force from a peak value at the moment when displacement of the to the hand-actuated selector 212 crosses the second threshold displacement $T_{D2}$, to a level that matches or approximately matches a force imparted during the first control state 772. More particularly, the haptic force decreases at a second rate relative to increasing displacement of the hand-actuated selector 212. The magnitude of the second rate is greater than a magnitude of the first rate. In an example system, the second rate has a magnitude selected to provide a user with a substantially instantaneous tactile indication that a click event has been triggered. In the example user input device 204 of FIG. 6A, a magnitude of a third feedback force during the third control state 776 is represented by the lengths of arrows 756a, 756b. Grip button 530a imparts force 764a in a first direction to index finger 758, and grip button 530b imparts force 756b in a second direction opposite to the first direction to thumb 760. In an example system, the control function returns to the first control state 772 in response to the one or more sensors 247b providing signals to indicate when the displacement returns to the neutral displacement distance, the third control state 776.

In an example user input device 204, the selector 212 impacts a stop surface at or about the moment that the hand-actuated selector 212 reaches the third threshold displacement $T_{D3}$ at control stage 778. In the example input device 204 of FIG. 6A, the hand-actuated selector 212 includes the displaceable grip buttons 530a, 530b and the handle 530 acts as a stop surface. The impact of the hand-actuated selector 212 upon the stop surface provides an abrupt reactive force that provides an additional tactile sensation to a user indicating that the click event is complete and that the hand-actuated selector 212 is ready to return to the second control state 772, which is the rest or neutral state. Thus, the stop surface 530, provides haptic feedback when the control function 700 has in effect, returned to the first control state 772 in which the one or more motors 545 provide a maintaining force.

Figure 8:
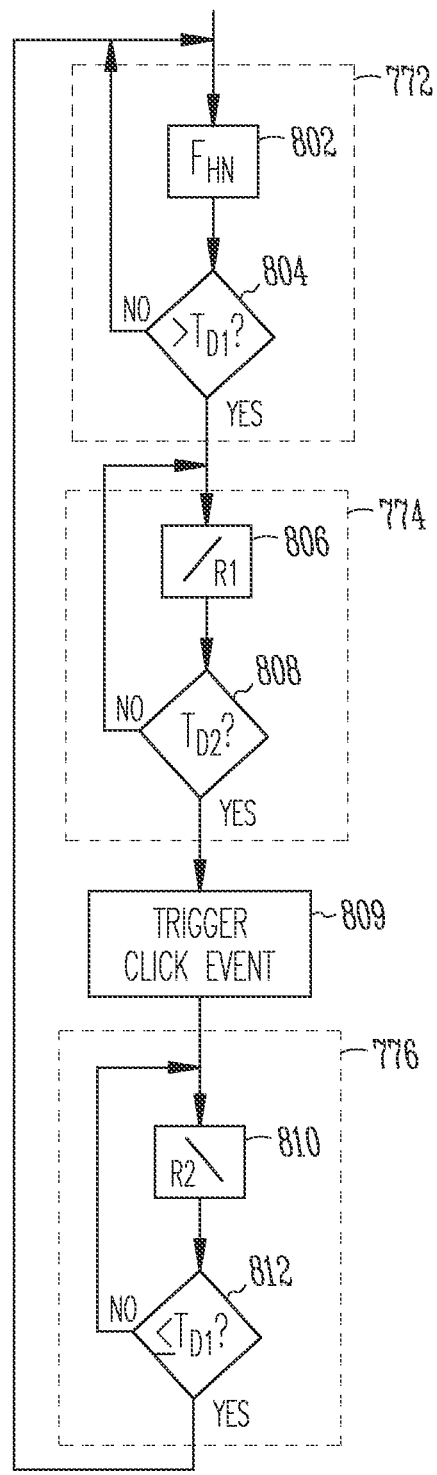
FIG. 8 is an illustrative flow diagram representing a control process to control provision of haptic force and triggering of a click event based upon displacement of a hand-actuated selector relative to the user input device.

FIG. 8 is an illustrative flow diagram representing a control process 800 according to the control function of FIG. 7 to control provision of force and triggering of a click event based upon displacement of a hand-actuated selector 212 relative to the user input device 204. The input controller 118 includes one or more processor circuits programmed with executable instructions to implement the control process 800. At operation 802 during the first control state 772, the input controller 118 causes the one or more motors 545 to provide a neutral maintaining force ($F_{HN}$) to the hand-actuated selector 212 while the one or more second sensors 547b indicate that a user has provided no second user input motion 654 causing the hand-actuated selector 212 to be displaced by at least a first threshold distance $T_{D1}$ from a neutral position. A first threshold decision operation 804 monitors the one or more second sensors 547b to detect when the displacement of the hand-actuated selector meets the first threshold displacement TD. In the example hand-actuated selector 212 of FIG. 6A, the first threshold decision operation 804 determines when displacement position of the grip buttons 530a, 530b from their neutral position meets the first displacement threshold. An example input controller 118 provides a motor control signal causing the one or more motors 545 to produce zero magnitude haptic force while the selector 212 is displaced by less than the first threshold haptic distance; a biasing member such as a spring maintains the selector 212 in the neutral position while the selector 212 is displaced by less than the first threshold haptic distance.

The control process transitions to the second control state 774 in response to the displacement meeting the first threshold displacement distance $T_{D1}$. The process 800 remains in the first control state 772 while displacement does not yet meet the first threshold displacement distance. At operation 806 during the second control state 774 the input controller 118 causes the one or more motors 545 to impart a haptic feedback force to the hand-actuated selector 212 that increases at a first rate that is a function of increasing displacement of the grip buttons from the neutral position. In an example system, operation 806 can set a rate of buildup of haptic feedback force to vary as a linear or non-linear function of displacement, for example. A second threshold decision operation 808 monitors the one or more second sensors 547b to detect when the displacement of the hand-actuated selector meets the second threshold displacement $T_{D2}$. In the example hand-actuated selector 212 of FIG. 6A, the second threshold decision operation 808 determines when displacement position of the grip buttons 530a, 530b from their neutral position meets the second displacement threshold distance.

The control process transitions to a third control state 776 in response to the displacement meeting the second threshold displacement distance $T_{D2}$. The process 800 remains in the second control state 774 while displacement does not yet meet the second threshold displacement distance. At operation 809, the input controller 118 sends a control signal to the display system 120 to trigger an occurrence of a click event. At operation 810, during the third control state 776 the input controller 118 causes the one or more motors 545 to impart a haptic feedback force to the hand-actuated selector 212 that decreases at a second rate from a peak value when transiting from the second to the third control state to a level that matches or approximately matches a force imparted during the first control state 772. The magnitude of the second rate is greater than a magnitude of the first rate. During decision operation 812, the input controller 118 monitors sensor signals provided by the one or more sensors 547b to determine when the displacement of the selector 212 meets (e.g., less than or equal to) the first threshold displacement $T_{D1}$. In response to the displacement meeting the first displacement distance, control process 800 transitions back to operation 802.

Variation in haptic force during the first, second and third control states provides a user with tactile indications of the status of a click event. During the second control state 774, the buildup of haptic force indicates to a user that a trigger event is increasingly imminent. During the third control state 776, a swift decrease in haptic force indicates the triggering of a click event. During the first control state 772, a maintaining force maintains the hand-held reinforces to a user that the haptic event has occurred. A hard stop at a physical stop surface 530 indicates to a user return that the hand-actuated selector 212 has returned to the neutral first control state 772.

Isolating Cursor Motion from Push Button Motion

During operation of the display system 120 in the second (2D) mode, digits of a user's hand can be used to select a control element displayed in the viewing plane 502. During operation second mode, the input controller 118 causes motion of a cursor 402 in the graphical user interface displayed in the viewing plane 502 to follow motion of a user input device 204 in the haptic plane 504. Cartesian coordinate locations in the viewing plane 502 correspond to cartesian coordinate locations in the haptic plane 504. A user selects a control element, by first, moving user input device 204 to a coordinate location in the haptic plane 504 that corresponds to a control element coordinate location in the viewing plane 502 to visually align the cursor 402 with the control element, and by second, imparting an actuation motion to the hand-actuated selector 212. A user's fingers can impart motion to a hand-actuated selector 212 to increase its displacement from a neutral position to trigger a click event as described above with reference to FIGS. 7-8, for example.

Motion of a user's fingers can influence motion of the rest of a user's hand. Referring to the example hand-actuated selector 212 of FIG. 6A, when a user imparts a closure force to the grip buttons 530a, 530b to implement a click, the user's finger motion can cause a corresponding motion of the controller 204 on which the grip buttons 530a, 530b are mounted. A user-imparted motion of the grip buttons 530a. 530b can result in a slight unintended change, or jump, in position of the controller 204. Such unintended change in position of the controller 204 in the haptic plane 504 can cause a corresponding unintended change in position of the cursor 402 in the viewing pane 502. As a result, when the grip buttons 530a, 530b are used for clicking on a control element in a graphical user interface menu, for example, the cursor 402 can tend to jump over the control element during the clicking process. Thus, a user's sudden actuating a click event can cause a sudden unintended jump in cursor movement resulting in misalignment of cursor with a target control element, which can result in selection of an erroneous target. This can be particularly frustrating if a targeted clickable control element is not large and the user ends up missing the targeted element.

A missed target can be especially deleterious in a surgical environment. For example, the viewing plane 502 can display a pre-operative MRI or CT scan instead of or in addition to control elements. A target element with which a surgeon user intends to visually align the cursor for selection may be a delicate anatomical feature, such as a nerve or a blood vessel, for example. The surgeon may intend to enlarge the view of the feature or to transition to other anatomical features represented in the MRI or CT scan that are located above or below the targeted feature. Thus, precision alignment between cursor and target element may be required.

Referring again to the control system of FIG. 6B, an example input controller 118 is configured to compute a motion transform function to provide to the display system 120 on line 561, a cursor motion control signal that indicates motion of the user input device 204 sensed by the one or more first sensors 547a, the first cursor motion input signal and the second cursor motion input signal. The display system displays motion of the cursor 402 within the graphical user interface 400 that follows motion of the user input device 204.

Figure 9:
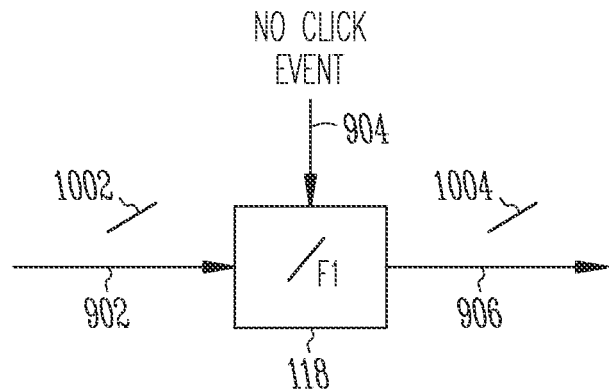
FIG. 9 is an illustrative diagram representing a configuration of the input controller to implement a first transform in absence of a click event.
Figure 10:
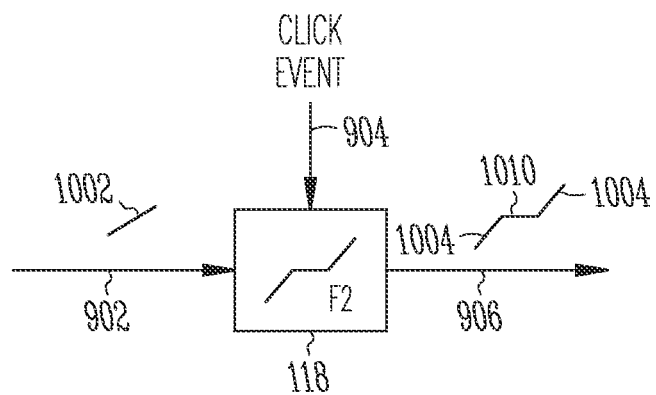
FIG. 10 is an illustrative diagram representing a configuration of the controller the input controller to implement a second transform in presence of a click event.

In an example user input device 204, a click event typically involves rapid movement of a hand-actuated selector 212. The controller system 118 is configured with instructions to adjust transform functionality during an occurrence of user motion input to a hand-actuated selector 212 that is mounted to the user input device 204 to effect a click event where such user motion input also could influence motion of the user input device. FIG. 9 is an illustrative diagram representing a configuration of the input controller 118 to implement a first transform F1 in absence of a click event. FIG. 10 is an illustrative diagram representing a configuration of the controller the input controller 118 to implement a second transform F2 in presence of a click event.

Referring to FIG. 9, based on the input controller 118 determining that motion of a user's digits (e.g., fingers and/or thumbs) and/or overall hand motion indicates that the user is not in the process of causing a launch of a click event signal, the input controller 118 imparts a first transform function F1 that causes motion of a cursor 402 in the viewing plane 502 to follow motion of a user input device 204 in the haptic plane 504. More particularly, an example input controller 118 is configured to cause cartesian coordinates of the cursor 402 in the viewing plane 502 to match cartesian coordinates of the user input device 204 in the haptic plane 504. Moreover, in the absence of a click event, an example input controller 118 can scale motion of the user input device 204 to motion of the cursor 402 by a prescribed amount. For example, an input controller 118 can be calibrated for a predetermined one-to-one (1:1) movement ratio of user input device motion to cursor motion in which, distance that the user input device 204 moves in the haptic plane 504 exactly matches distance by which the cursor 402 moves in the viewing plane 502. Alternatively, for example, the input controller 118 can be calibrated for a predetermined two-to-one (2:1) movement ratio in which, distance that the user input device 204 moves in the haptic plane 504 exactly twice distance by which the cursor 402 moves in the viewing plane 502.

Referring to FIG. 10, based on the input controller 118 determining that motion of a user's digits (e.g., fingers and/or thumbs) and/or overall hand motion indicates that the user is in the process of causing a launch a click event, the input controller 118 imparts a second transform function F2 that reduces the ratio of cursor movement in response to user input device movement during a time interval when a user is causing a launch of a click event. The reduced movement ratio results in reduction in cursor motion in the viewing plane 502 during a click in response to user input device motion in the haptic plane 504.

Figure 11:
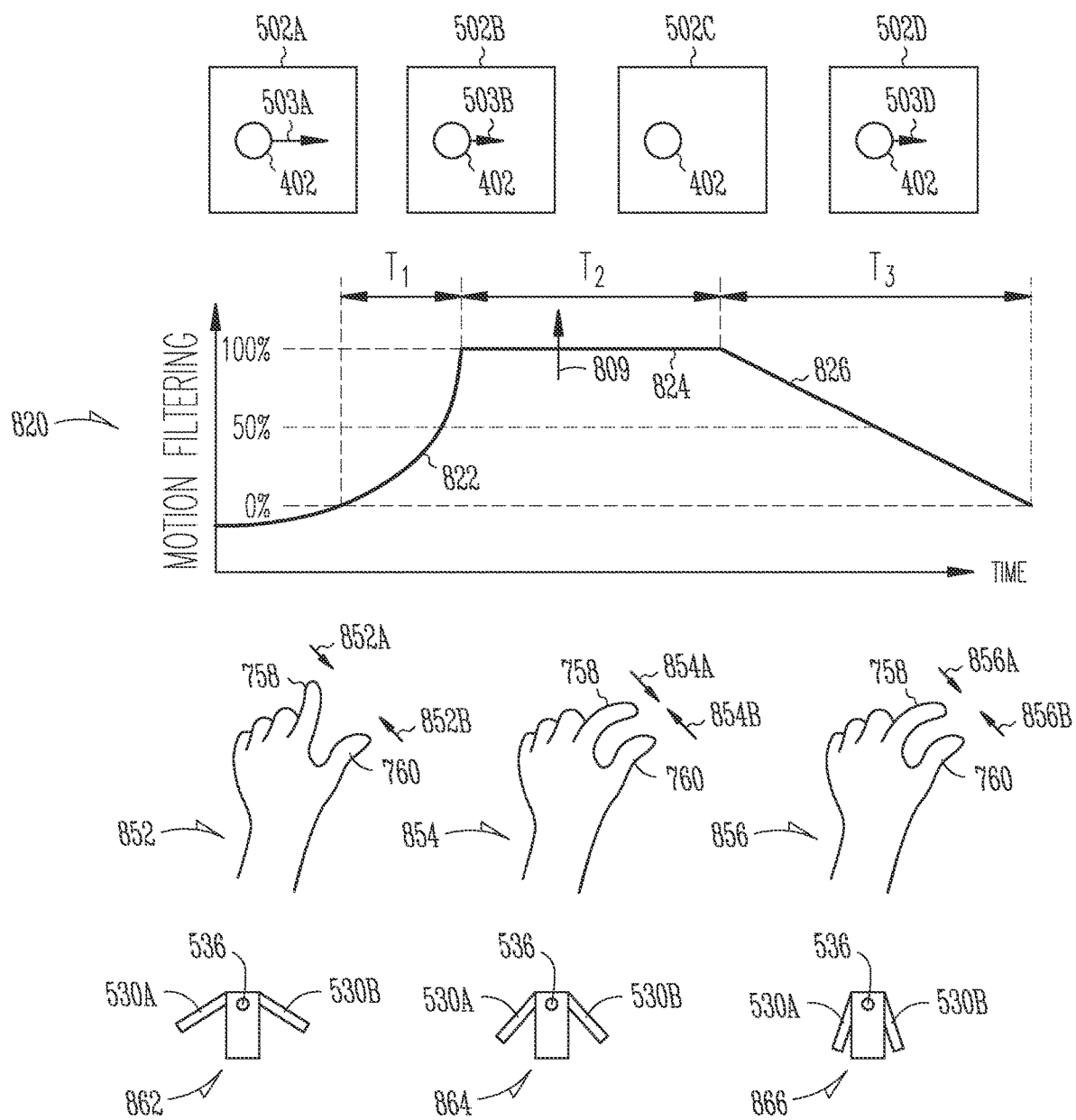
FIG. 11 is an illustrative drawing showing a second control function curve representing an example second transform function to determine controller motion filtering versus time during a click event and also showing a time-aligned sequence of grip button displacements, a time-aligned with a sequence of hand formations, and a time-aligned sequence of viewing plane instances.

FIG. 11 is an illustrative drawing showing a second control function curve 820 representing an example second transform function F2 to determine controller motion filtering versus time during a click event and also showing a time-aligned sequence of grip button displacements, a time-aligned with a sequence of hand formations, and a time-aligned sequence of viewing plane instances. As used herein, selector velocity refers to rate of increase in displacement from a neutral position of the hand-actuated selector 212 relative to a base of a user input device 204. In the example case of FIG. 6A, selector velocity refers to rate of increase in displacement of the grip buttons 530a, 530b relative to the handle 530. As used herein, an increase in controller motion filtering corresponds to a decrease in a ratio of movement of motion of a user input device 204 to motion of a cursor 402. That is, the greater the magnitude controller motion filtering the less a movement of the input device 204 in the haptic plane 504 causes a corresponding movement of the cursor 402 in the viewing plane 502.

The example second transform function F2 includes first, second, and third filtering functions. As depicted by the second control function curve 820, the input controller 118 is configured to impart a first filtering function 822 that spans a first time interval, $T_1$, during which displacement of a hand-actuated selector 212 from a neutral position relative to the user input device 204 changes at a rate that is less than a first threshold displacement rate ($T_{R1}$). As depicted by the second control function curve 820, the input controller 118 is configured to impart a second filtering function 824 that spans a second time interval $T_2$ during which displacement of a hand-actuated selector 212 from a neutral position relative to the user input device 204 changes at a rate that is equal to or greater than the first threshold rate $T_{R1}$. As depicted by the second control function curve 820, the input controller 118 is configured to impart a third filtering function 826 spans a third time interval $T_3$, following the second time interval $T_2$, when grip buttons 530a, 530b continue to move but at a rate that is no longer equal to or greater than the first threshold rate $T_{R1}$. In the case of the example selector 212 of FIG. 6A, displacement of the grip buttons 530a, 530b from their neutral positions relative to the handle 530 increases during each of the first, second, and third time intervals.

Referring to the second control function curve 820, during the first time interval $T_1$, while the hand-actuated selector 212 move relative to the user input device 204 (e.g., grip buttons 530a, 530b move relative to handle 530) at a rate less than a $T_{R1}$, the first filtering function 822 increases user input device motion filtering in correspondence with increasing rate of input device motion; the faster the hand-actuated selector 212 moves relative to the input device 204 (e.g., the faster the grip buttons 530a, 530b move relative to the handle 530), the less a movement of the user input device 204 effects a corresponding movement of the cursor 402, which corresponds to a reducing of the movement ratio with increasing rate of grip button movement. Thus, motion of the cursor 402 follows motion of the user input device 204 according to a first dynamic movement ratio during the first time interval $T_1$. Referring to the example of FIG. 6A and to FIG. 11, direction of arrows 852a, 852b indicates lessening of displacement distance between the fingers 758, 760 and between grip buttons 530a, 530b. The length of the arrows 852a, 852b indicate rate at which the grip buttons are moving closer together. An example input controller 118 can be configured to use the first filtering function 822 to increase user input device motion filtering (which correspondingly decreases the movement ratio) as a linear function of time, a logarithmic function of time or an exponential function of time, for example. Thus, during the first time interval $T_1$, while the selector displacement rate is less than the first threshold rate $T_{R1}$, filtering of user input device motion increases with increasing selector rate.

During the second time interval $T_2$, while hand-actuated selector 212 moves relative to the selector at a rate equal than or greater than the first threshold rate $T_{R1}$, the second filtering function 822 causes a substantially constant minimal movement ratio. In an alternative example surgical system 100, while hand-actuated selector 212 moves relative to the selector at a rate equal than or greater than the first threshold rate $T_{R1}$, the second filtering function 822 causes motion of the cursor 402 to stop such that the cursor motion does not follow motion of the user input device 204. Referring to the example of FIG. 6A and to FIG. 11, direction of arrows 854a, 854b indicates lessening of displacement distance between the fingers 758, 760 and between grip buttons 530a, 530b. Since the grip buttons 530a, 530b are moving at a faster rate during the second time interval $T_2$ than during the first time interval, arrows 854a, 854b have greater length than arrows 852a, 852b. An example input controller 118 can be configured to cause the movement ratio to be zero during the second time interval. That is, the cursor 402 does not move in response to movement of the controller 204. More particularly, for example, an example input controller 118 can be configured to cause cursor motion to stop during the second time interval $T_2$, (i.e. transition to a movement ratio 1:0). Alternatively, for example, an example input controller 118 can be configured to cause a movement ratio decrease to 1:0.1 during the second time interval $T_2$. Thus, during the second time interval $T_2$, the filtering of user input device motion and the corresponding movement ratio remain constant while the rate of movement of the grip buttons 530a, 530b is at or exceeds $T_{R1}$. A duration of the second time interval $T_2$ is determined based upon length of time that the rate of movement of the selector 212 530a, 530b matches or exceeds the first threshold rate $T_{R1}$.

In an example surgical system 100, a click event 809 is triggered during the second time interval T2. The triggering of a click event can be controlled according to the first control function curve 720 of FIG. 7 and the control process 800 of FIG. 8, for example.

During the third time interval $T_3$, when rate of movement of the hand-actuated selector 212 decreases to a rate less than a $T_{R1}$, the third filtering function 826 causes decrease in controller motion filtering as a function of time, which corresponds to an increase of the movement ratio as a function of time. Thus, motion of the cursor 402 follows motion of the user input device 204 according to a second dynamic movement ratio during the third time interval $T_3$. Referring to the example hand actuated selector 212 and user input device 204 of FIG. 6A, since the rate of movement of grip buttons 530a, 530b relative to handle 530 is greater during the second time interval $T_2$ than during the third time interval $T_3$, arrows 856a, 856b have shorter length than arrows 854a, 854b. An example input controller 118 can be configured to use the third filtering function 826 to decrease controller motion filtering (which correspondingly increases the movement ratio) as a linear function of time, a logarithmic function of time or an exponential function of time, for example. Moreover, an example input controller 118 can be configured to use the third filtering function 826 to cause the movement ratio to increase as a function of time until it regains a pre-click movement ratio of 1:1, for example. Thus, during the third time interval $T_3$, the filtering of user input device motion decreases with time, which means that the movement ratio increases with time.

Still referring to FIG. 11, the sequence of viewing window display instances 502a, 502b, 502c, 502d pictorially represent changes in in cursor rate of movement within the viewing plane 502 at different points along the second control function curve 820. In each sequential viewing window instances 502a, 502b, 502c, 502d, a respective a respective arrow 503a, 503b, 503d is associated with the cursor 402. A length of the respective arrow in each respective viewing window display instance represents a magnitude of the movement ratio, the ratio of user input device motion to corresponding cursor motion, during the display time of respective viewing window.

Before start of an example click event, the movement ratio filter function to impart a maximum value movement ratio represented by long length of the respective arrow 503a in respective viewing window display 502a.

During the first time interval $T_1$, in response to movement of the hand-actuated selector 212 relative to the user input device 204 at a rate less than a TR, the example input controller 118 is configured by the second transform function F2 to increase in user input device motion filtering as a function of rate of movement of the hand-actuated selector 212 relative to the user input device 204, which corresponds to a reducing of the movement ratio with increasing rate of decrease of grip button displacement. The reduction in movement ratio is represented by the shorter length of arrow 503b in the viewing window display 502b.

During the second time interval $T_2$, in response to the hand-actuated selector 212 moving relative to the user input device 204 at a rate equal to or greater than $T_{R1}$, the input controller 118 is configured by the second transform function F2 to cause a constant minimal movement ratio despite a continued increase in the rate of movement. The minimal movement ratio is represented by the absence of an arrow in the viewing window display 502c.

During the third time interval $T_3$, in response to movement of the hand-actuated selector 212 relative to the user input device 204 at a decreased rate that no longer is equal to or greater than $T_{R1}$, the input controller 118 is configured by the second transform function F2 to cause a decrease in controller motion filtering (which correspondingly increases the movement ratio) as a function of time. The increase in movement ratio is represented by the reappearance and of arrow 503d in the viewing window display 502d. It is noted that the shorter length of the arrow 503d indicates that the movement ratio has not yet returned to the pre-click level.

Computer Hardware and Storage Devices

Figure 12:
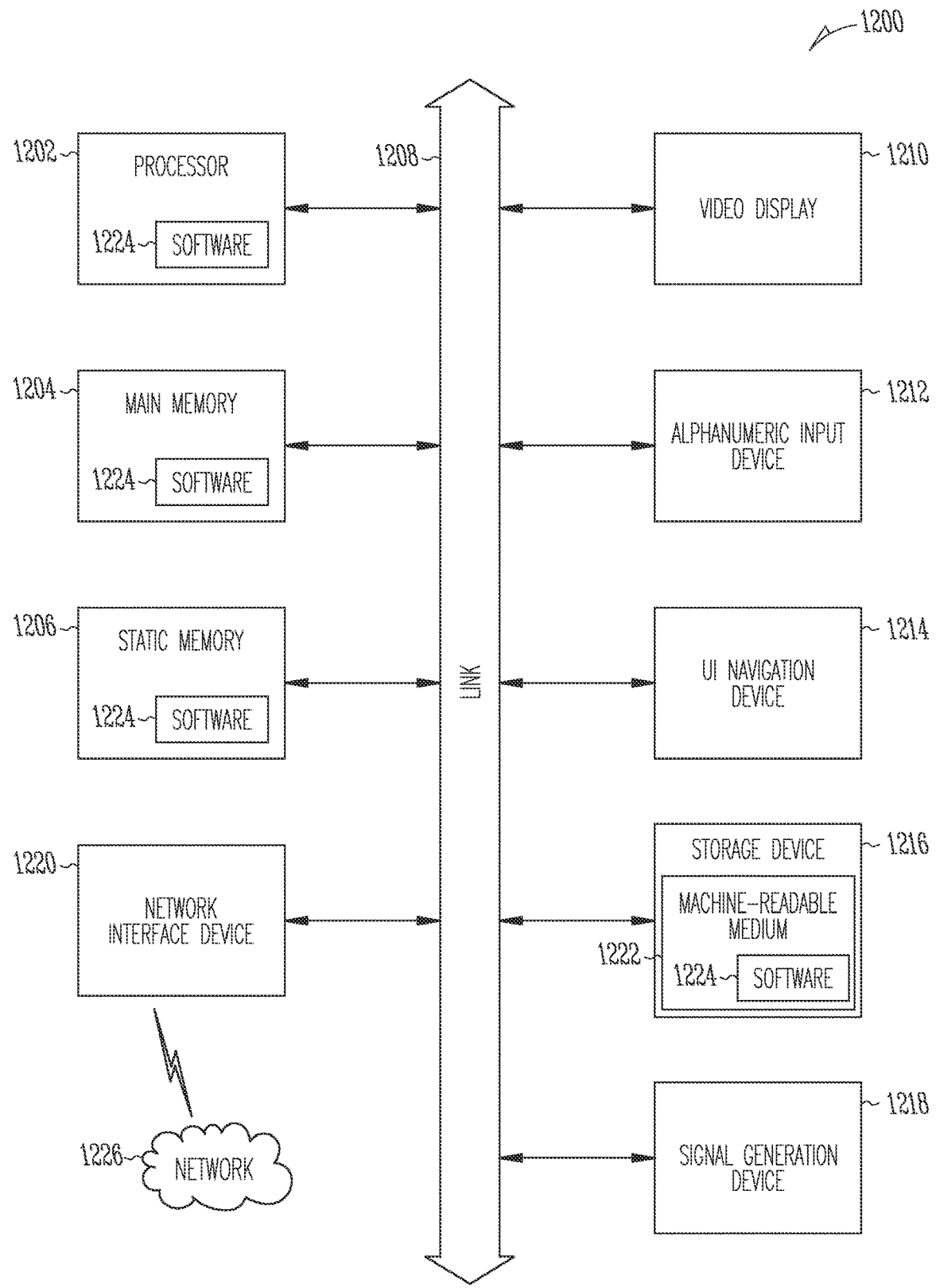
FIG. 12 is an illustrative block diagram of an example computer system.

FIG. 12 is an illustrative block diagram showing an example machine upon which any one or more of the techniques (e.g., methodologies) discussed herein may perform, according to an example embodiment. FIG. 12 shows an illustrative diagrammatic representation of a more particularized computer system 1200, which can be used to implement the controller system 118, for example. The computer system 1200 can be configured to implement, for example, a computerized training module. In alternative embodiments, the computer system 1200 operates as a standalone device or may be connected (e.g., networked) to other machines. In a networked deployment, the computer system 1200 may operate in the capacity of a server or a client machine in server-client network environment, or as a peer machine in a peer-to-peer (or distributed) network environment. The computer system 1200 may be a server computer, a client computer, a personal computer (PC), a tablet PC, a Personal Digital Assistant (PDA), a cellular telephone, or any machine capable of executing a set of instructions (sequential or otherwise) that specify actions to be taken by that machine. Further, while only a single machine (i.e., computer system 1200) is illustrated, the term "machine" shall also be taken to include any collection of machines that individually or jointly execute a set (or multiple sets) of instructions to perform any one or more of the methodologies discussed herein.

The example computer system 1200 includes a processor 1202 (e.g., a central processing unit (CPU), a graphics processing unit (GPU), or both), a main memory 1204 and a static memory 1206, which communicate with each other via a bus 1208. The computer system 1200 may further include a video display unit 1210 (e.g., liquid crystal display (LCD), organic light emitting diode (OLED) display, touch screen, or a cathode ray tube (CRT)) that can be used to display positions of the surgical instrument 124 and flexible instrument 120, for example. The computer system 1200 also includes an alphanumeric input device 1212 (e.g., a keyboard, a physical keyboard, a virtual keyboard using software), a cursor control device or input sensor 1214 (e.g., a mouse, a track pad, a trackball, a sensor or reader, a machine readable information reader, bar code reader), a disk drive unit 1216, a signal generation device 1218 (e.g., a speaker) and a network interface device or transceiver 1220.

The disk drive unit 1216 includes a non-transitory machine-readable storage device medium 1222 on which is stored one or more sets of instructions 1224 (e.g., software) embodying any one or more of the methodologies or functions described herein. The instructions 1224 may also reside, completely or at least partially, within the main memory 1204, static memory 1206 and/or within the processor 1202 during execution thereof by the computer system 1200, the main memory 1204 and the processor 1202 also constituting non-transitory machine-readable storage device media. The non-transitory machine-readable storage device medium 1222 also can store an integrated circuit design and waveform structures. The instructions 1224 may further be transmitted or received over a network 1226 via the network interface device or transceiver 1220. While the machine-readable storage device medium 1222 is shown in an example embodiment to be a single medium, the term "machine-readable medium," "computer readable medium," and the like should be taken to include a single medium or multiple media (e.g., a centralized or distributed database, and/or associated caches and servers) that store the one or more sets of instructions 1224. The term "machine-readable medium" shall also be taken to include any medium that is capable of storing, encoding or carrying a set of instructions for execution by the machine and that cause the machine to perform any one or more of the methodologies of the present disclosure. The term "machine-readable medium" shall accordingly be taken to include, but not be limited to, solid-state memories, optical and magnetic media, and carrier wave signals It will be appreciated that, for clarity purposes, the above description may describe some embodiments with reference to different functional units or processors. However, it will be apparent that any suitable distribution of functionality between different functional units, processors or domains may be used without detracting from the present disclosure. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Although the present disclosure has been described in connection with some embodiments, it is not intended to be limited to the specific form set forth herein. One skilled in the art would recognize that various features of the described embodiments may be combined in accordance with the present disclosure. Moreover, it will be appreciated that various modifications and alterations may be made by those skilled in the art without departing from the scope of the present disclosure.

In addition, in the foregoing detailed description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the detailed description, with each claim standing on its own as a separate embodiment.

The foregoing description and drawings of embodiments in accordance with the present invention are merely illustrative of the principles of the inventive subject matter. Therefore, it will be understood that various modifications can be made to the embodiments by those skilled in the art without departing from the scope of the inventive subject matter, which is defined in the appended claims.

Thus, while certain exemplary embodiments of the invention have been described and shown in the accompanying drawings, it is to be understood that such embodiments are merely illustrative of and not restrictive on the broad inventive subject matter, and that the embodiments of the invention not be limited to the specific constructions and arrangements shown and described, since various other modifications may occur to those ordinarily skilled in the art.

VARIOUS EXAMPLES

Example 1 can include a method to control actuation of a click event by a hand-actuated selector moveably mounted to a mount structure, comprising: using one or more sensors to sense amount of displacement distance of the hand-actuated selector from a neutral position; in response to the hand-actuated sensor at a displacement distance less than a first threshold distance from the neutral position, controlling one or more motors according to a first control state to impart a maintaining force; in response to sensing the hand-actuated sensor at a displacement distance between a first threshold distance from the neutral position neutral position and a second threshold distance from the neutral position, controlling one or more motors according to a second control state to impart a haptic force to the hand-actuated selector that increases as a function of increasing displacement of the hand-actuated selector from the neutral displacement position; in response to sensing the hand-actuated sensor has met the second threshold distance from the neutral position, imparting a click event signal to cause an occurrence of the click event at a display system, and controlling the one or more motors according to a third control state to a reduce magnitude of the haptic force imparted to the hand-actuated selector to a reduced magnitude that is less than a maximum magnitude of the haptic force imparted during the second control state.

Example 2 can include the subject matter of Example 1, wherein the maintaining force is zero.

Example 3 can include the subject matter of Example 1, wherein the maintaining force is less than a haptic force imparted by the one or more motors according to the second control state.

Example 4 can include the subject matter of Example 1, wherein controlling the one or more motors according to the third control state includes controlling the one or more motors to impart a haptic force to the hand-actuated selector that decreases in magnitude to the reduced magnitude as a function of increasing displacement of the hand-actuated selector from the neutral displacement position.

Example 5 can include the subject matter of Example 4, wherein controlling the one or more motors according to the second control state includes controlling the one or more motors to increase magnitude of the haptic force at a first rate; and wherein controlling the one or more motors according to the third control state includes controlling the one or more motors to decrease magnitude of the haptic force at a second rate; and wherein a magnitude of the first rate is less than a magnitude of the second rate.

Example 6 can include the subject matter of Example 4, wherein controlling the one or more motors according to the third control state includes controlling the one or more motors to impart a haptic force to the hand-actuated selector that decreases in magnitude to the reduced magnitude as a function of increasing displacement of the hand-actuated selector from the neutral displacement position.

Example 7 can include the subject matter of Example 4 wherein controlling the one or more motors according to the third control state includes controlling the one or more motors to impart a haptic force to the hand-actuated selector that decreases instantaneously to the reduced magnitude.

Example 8 can include the subject matter of Example 1 further including: using the one or more motors to cause the hand-actuated selector to move to the neutral position.

Example 9 can include the subject matter of Example 1, further including: using a resilient member to cause the hand-actuated selector to move to the neutral position.

Example 10 can include the subject matter of Example 1, further including: using a stop surface to stop motion of the hand-actuated selector.

Example 11 can include the subject matter of Example 1, further including: using a stop surface at the mount structure to stop motion of the hand-actuated selector.

Example 12 can include the subject matter of Example 1, further including: using a stop surface, positioned to impart a reactive force to the hand-actuated selector to stop further displacement of the hand-actuated selector when the hand-actuated selector reaches the third threshold displacement distance from the neutral position.

Example 13 can include the subject matter of Example 1, further including: controlling the one or more motors according to a third control state to impart the reduced magnitude to the hand-actuated selector at displacement distances between a displacement distance at which the reduced magnitude is first imparted to the hand-actuated selector and the third threshold distance.

Example 14 can include the subject matter of Example 1, wherein the one or more sensors are configured to sense displacement of the hand-actuated selector relative to the mount structure.

Example 15 can include the subject matter of Example 1, wherein using the one or more sensors to sense amount of displacement of the hand-actuated selector from a neutral position during movement of the hand-actuated selector.

Example 16 can include an apparatus to control actuation of a click event by a hand-actuated selector moveably mounted to a mount structure, comprising: one or more sensors configured to sense position of the hand-actuated selector; one or more motors configured to impart haptic force to the hand-actuated selector; processing circuitry; and a memory system storing instructions which, when executed by the processing circuitry, cause the processing circuitry to perform operations comprising: using the one or more sensors to sense amount of displacement of the hand-actuated selector from a neutral position; in response to the hand-actuated sensor at a displacement distance less than a first threshold distance from the neutral position, controlling one or more motors according to a first control state to impart a maintaining force; in response to sensing the hand-actuated sensor at a displacement distance between the first threshold distance from a neutral position neutral position and a second threshold distance from the neutral position, controlling one or more motors according to a second control state to impart a haptic force to the hand-actuated selector that increases in magnitude as a function of increasing displacement of the hand-actuated selector from the neutral displacement position; in response to sensing the hand-actuated sensor has met the second threshold distance from the neutral position, imparting a click event signal to cause an occurrence of the click event at a display system, and controlling the one or more motors according to a third control state to impart a haptic force to the hand-actuated selector that decreases in magnitude to a reduced magnitude as a function of increasing displacement of the hand-actuated selector from the neutral displacement position, the reduced magnitude being less than a maximum magnitude of the haptic force imparted during the second control state; and controlling the one or more motors according to a third control state to a reduce magnitude of the haptic force imparted to the hand-actuated selector to a reduced magnitude that is less than a maximum magnitude of the haptic force imparted during the second control state.

Example 17 can include the subject matter of Example 16, wherein the maintaining force is zero.

Example 18 can include the subject matter of Example 16, wherein the maintaining force is less than a haptic force imparted by the one or more motors according to the second control state.

Example 19 can include the subject matter of Example 16, wherein the act of controlling the control the one or more motors according to the third control state occurs after the act of imparting the click event signal.

Example 20 can include the subject matter of Example 16, wherein controlling the one or more motors according to the third control state includes controlling the one or more motors to impart a haptic force to the hand-actuated selector that decreases in magnitude to the reduced magnitude as a function of increasing displacement of the hand-actuated selector from the neutral displacement position.

Example 21 can include the subject matter of Example 20, wherein controlling the one or more motors according to the second control state includes controlling the one or more motors to increase magnitude of the haptic force at a first rate; and wherein controlling the one or more motors according to the third control state includes controlling the one or more motors to decrease magnitude of the haptic force at a second rate; and wherein a magnitude of the first rate is less than a magnitude of the second rate.

Example 22 can include the subject matter of Example 20, wherein controlling the one or more motors according to the third control state includes controlling the one or more motors to impart a haptic force to the hand-actuated selector that decreases in magnitude to the reduced magnitude as a function of increasing displacement of the hand-actuated selector from the neutral displacement position.

Example 23 can include the subject matter of Example 20, wherein controlling the one or more motors according to the third control state includes controlling the one or more motors to impart a haptic force to the hand-actuated selector that decreases instantaneously to the reduced magnitude.

Example 24 can include the subject matter of Example 16, further including: instructions that, when executed cause the processor to perform operations comprising: controlling the one or more motors to cause the hand-actuated selector to move to the neutral position.

Example 25 can include the subject matter of Example 16, further including: a resilient member configured to cause the hand-actuated selector to move to the neutral position.

Example 26 can include the subject matter of Example 16, further including: a stop surface configured to stop motion of the hand-actuated selector when the hand-actuated selector reaches the third threshold displacement distance from the neutral position.

Example 27 can include a method to control motion of a cursor in a first two-dimensional (2D) plane based upon motion of a user input device in a second 2D plane and based upon motion of a hand-actuated selector moveably mounted to the user input device, comprising: causing motion of the cursor in the first 2D plane to follow motion of the user input device in the second 2D plane according to a constant movement ratio, while the hand-actuated selector moves relative to the user input device at a rate less than a first threshold rate; causing motion of the cursor in the first 2D plane to follow motion of the user interface device in the second 2D plane according to a movement ratio that decreases as a function of increasing rate of movement of the hand-actuated selector relative to the user input device in response to rate of movement of the hand-actuated selector relative to the controller being between the first threshold rate and a second threshold rate; and causing motion of the cursor in the first 2D plane to follow motion of the user input device in the second 2D plane according to motion ratio that increases as a function of decreasing rate of movement of the hand-actuated selector relative to the user input device, in response to rate of movement of the hand-actuated selector relative to the user input device decreasing below the second threshold rate.

Example 28 can include the subject matter of Example 27, further including: controlling causing motion of the cursor in the first 2D plane to follow motion of the user input device in the second 2D plane according to a second constant movement ratio that is less than the first movement ratio, in response to the hand-actuated selector moving relative to the user input device at a rate greater than a second threshold rate.

Example 29 can include the subject matter of Example 27, further including: causing motion of the cursor in the first 2D plane to stop following motion of the user input device in the second 2D plane, in response to the hand-actuated selector moving relative to the user input device at a rate greater than a second threshold rate.

Example 30 can include an apparatus to control motion of a cursor in a first two-dimensional (2D) image display plane in a display system based upon motion of a user input device in a second 2D haptic plane and based upon motion of a hand-actuated selector moveably mounted to the user input device, comprising: one or more sensors configured to sense motion of the hand-actuated selector; processing circuitry; and a memory system storing instructions which, when executed by the processing circuitry, cause the processing circuitry to perform operations comprising: causing motion of the cursor in the first 2D plane to follow motion of the user input device in the second 2D plane according to a constant movement ratio, while the hand-actuated selector moves relative to the user input device at a rate less than a first threshold rate; causing motion of the cursor in the first 2D plane to follow motion of the user interface device in the second 2D plane according to a movement ratio that decreases as a function of increasing rate of movement of the hand-actuated selector relative to the user input device, in response to rate of movement of the hand-actuated selector relative to the user input device being between the first threshold rate and a second threshold rate; and causing motion of the cursor in the first 2D plane to follow motion of the user input device in the second 2D plane according to motion ratio that increases as a function of decreasing rate of movement of the hand-actuated selector relative to the user input device, in response to rate of movement of the hand-actuated selector relative to the user input device decreasing below the second threshold rate.

Example 31 can include the subject matter of Example 30, further including: instructions that, when executed, cause the processor to perform operations comprising: causing motion of the cursor in the first 2D plane to follow motion of the user input device in the second 2D plane according to a second constant movement ratio that is less than the first movement ratio, in response to the hand-actuated selector moving relative to the user input device at a rate greater than a second threshold rate.

Example 32 can include the subject matter of Example 30, further including: instructions that, when executed, cause the processor to perform operations comprising: causing motion of the cursor in the first 2D plane to stop following motion of the user input device in the second 2D plane, in response to the hand-actuated selector moving relative to the user input device at a rate greater than a second threshold rate.

The invention claimed is:

1. A method to control actuation of a click event by a hand-actuated selector moveably mounted to a mount structure, comprising:
   using one or more sensors to sense amount of displacement distance of the hand-actuated selector from a neutral position;
   in response to the hand-actuated sensor at a displacement distance less than a first threshold distance from the neutral position, controlling one or more motors according to a first control state to impart a maintaining force;
   in response to sensing the hand-actuated sensor at a displacement distance between a first threshold distance from the neutral position neutral position and a second threshold distance from the neutral position, controlling one or more motors according to a second control state to impart a haptic force to the hand-actuated selector that increases as a function of increasing displacement of the hand-actuated selector from the neutral displacement position;
   in response to sensing the hand-actuated sensor has met the second threshold distance from the neutral position, imparting a click event signal to cause an occurrence of the click event at a display system, and
   controlling the one or more motors according to a third control state to reduce magnitude of the haptic force imparted to the hand-actuated selector to a reduced magnitude that is less than a maximum magnitude of the haptic force imparted during the second control state, wherein the haptic force decreases in magnitude to the reduced magnitude as a function of increasing displacement of the hand-actuated selector from the neutral displacement position.

2. The method of claim 1,
wherein the maintaining force is zero.

3. The method of claim 1,
wherein the maintaining is less than a haptic force imparted by the one or more motors according to the second control state.

4. The method of claim 1 further including:
using the one or more motors to cause the hand-actuated selector to move to the neutral position.

5. The method of claim 1 further including:
using a resilient member to cause the hand-actuated selector to move to the neutral position.

6. The method of claim 1 further including:
using a stop surface to stop motion of the hand-actuated selector.

7. The method of claim 1 further including:
using a stop surface, positioned to impart a reactive force to the hand-actuated selector to stop further displacement of the hand-actuated selector when the hand-actuated selector reaches the third threshold displacement distance from the neutral position.

8. An apparatus to control actuation of a click event by a hand-actuated selector moveably mounted to a mount structure, comprising:
one or more sensors configured to sense position of the hand-actuated selector;
one or more motors configured to impart haptic force to the hand-actuated selector;
processing circuitry; and
a memory system storing instructions which, when executed by the processing circuitry, cause the processing circuitry to perform operations comprising:
using the one or more sensors to sense amount of displacement of the hand-actuated selector from a neutral position;
in response to the hand-actuated sensor at a displacement distance less than a first threshold distance from the neutral position, controlling one or more motors according to a first control state to impart a maintaining force;
in response to sensing the hand-actuated sensor at a displacement distance between a first threshold distance from a neutral position neutral position and a second threshold distance from the neutral position, controlling one or more motors according to a second control state to impart a haptic force to the hand-actuated selector that increases in magnitude as a function of increasing displacement of the hand-actuated selector from the neutral displacement position;
in response to sensing the hand-actuated sensor has met the second threshold distance from the neutral position,
imparting a click event signal to cause an occurrence of the click event at a display system, and
controlling the one or more motors according to a third control state to reduce magnitude of the haptic force imparted to the hand-actuated selector to a reduced magnitude that is less than a maximum magnitude of the haptic force imparted during the second control state, wherein the haptic force decreases in magnitude to the reduced magnitude as a function of increasing displacement of the hand-actuated selector from the neutral displacement position.

9. The apparatus of claim 8,
wherein the maintaining force is zero.

10. The apparatus of claim 8,
wherein the maintaining force is less than a haptic force imparted by the one or more motors according to the second control state.

11. The apparatus of claim 8,
wherein the act of controlling the control the one or more motors according to the third control state occurs after the act of imparting the click event signal.

12. The apparatus of claim 8,
wherein controlling the one or more motors according to the third control state includes controlling the one or more motors to impart a haptic force to the hand-actuated selector that decreases instantaneously to the reduced magnitude.

13. The apparatus of claim 8 further including:
instructions that, when executed cause the processor to perform operations comprising:
controlling the one or more motors to cause the hand-actuated selector to move to the neutral position.

14. The apparatus of claim 8 further including:
a resilient member configured to cause the hand-actuated selector to move to the neutral position.

15. The apparatus of claim 8 further including:
a stop surface configured to stop motion of the hand-actuated selector when the hand-actuated selector reaches the third threshold displacement distance from the neutral position.

* * * * *